(12) United States Patent
Azarbarzin et al.

(10) Patent No.: US 9,414,818 B2
(45) Date of Patent: Aug. 16, 2016

(54) SURGICAL INSTRUMENTS WITH IMPROVED DEXTERITY FOR USE IN MINIMALLY INVASIVE SURGICAL PROCEDURES

(71) Applicant: SurgiQuest, Inc., Milford, CT (US)

(72) Inventors: Kurt Azarbarzin, Fairfield, CT (US); Dominick Mastri, Bridgeport, CT (US); Ralph Stearns, Bozrah, CT (US)

(73) Assignee: SurgiQuest, Inc., Milford, CT (US)

( * ) Notice: Subject to any disclaimer, the term of this patent is extended or adjusted under 35 U.S.C. 154(b) by 0 days.

(21) Appl. No.: 14/596,695

(22) Filed: Jan. 14, 2015

(65) Prior Publication Data
US 2015/0126977 A1   May 7, 2015

Related U.S. Application Data

(60) Division of application No. 13/940,446, filed on Jul. 12, 2013, now Pat. No. 8,961,396, and a division of application No. 12/789,643, filed on May 28, 2010, now abandoned, and a continuation of application No. PCT/US2008/085081, filed on Nov. 28, 2008.

(60) Provisional application No. 60/991,150, filed on Nov. 29, 2007, provisional application No. 61/053,038, filed on May 14, 2008, provisional application No. 61/091,335, filed on Aug. 22, 2008, provisional application No. 61/104,532, filed on Oct. 10, 2008.

(51) Int. Cl.
| | |
|---|---|
| *A61B 1/32* | (2006.01) |
| *A61B 17/00* | (2006.01) |
| *A61B 17/32* | (2006.01) |
| *A61B 17/29* | (2006.01) |
| *A61B 17/072* | (2006.01) |

(52) U.S. Cl.
CPC ........... *A61B 17/00234* (2013.01); *A61B 17/29* (2013.01); *A61B 17/320016* (2013.01); *A61B 17/07207* (2013.01); *A61B 2017/00367* (2013.01); *A61B 2017/00738* (2013.01); *A61B 2017/00946* (2013.01); *A61B 2017/291* (2013.01); *A61B 2017/2904* (2013.01); *A61B 2017/2905* (2013.01); *A61B 2017/2927* (2013.01); *A61B 2017/2929* (2013.01); *A61B 2017/2932* (2013.01)

(58) Field of Classification Search
CPC .................... A61B 17/320016; A61B 17/3423
USPC ................................................. 600/207–208
See application file for complete search history.

(56) References Cited

U.S. PATENT DOCUMENTS 5,224,930 A * 7/1993 Spaeth ............. A61B 17/00234
604/156
5,261,905 A * 11/1993 Doresey, III ....... A61B 18/1482
606/41

(Continued)

*Primary Examiner* — Ellen C Hammond
*Assistant Examiner* — Stuart S Bray
(74) *Attorney, Agent, or Firm* — Locke Lord LLP; Scott D. Wofsy

(57) ABSTRACT

A surgical instrument adapted and configured for use in minimally invasive surgical procedures includes a shaft, an end effector and a proximal handle. The longitudinal shaft has proximal and distal end portions, and defines a longitudinal axis of the surgical instrument. The distal end effector is connected to the distal end portion of the shaft, and is adapted and configured for performing a surgical task. The proximal handle portion is operably connected to the proximal end portion of the longitudinal shaft and has an actuatable portion operably connected to the end effector to result in movement of the end effector. The distal end portion of the shaft can be laterally offset from the longitudinal axis of the shaft and/or have one or more bends or curves formed therein. The proximal portion of the shaft can include at least one bend to allow for comfortable positioning of a surgeon's hands.

14 Claims, 16 Drawing Sheets

(56) References Cited

U.S. PATENT DOCUMENTS

| | | | | |
|---|---|---|---|---|
| 5,584,803 A * | 12/1996 | Stevens | A61B 17/29 | 604/101.01 |
| 5,658,307 A * | 8/1997 | Exconde | A61B 17/00234 | 606/190 |
| 5,667,473 A * | 9/1997 | Finn | A61B 1/00165 | 385/117 |
| 6,705,989 B2 * | 3/2004 | Cuschieri | A61B 17/0218 | 600/208 |
| 7,850,600 B1 * | 12/2010 | Piskun | A61B 1/05 | 600/114 |
| 8,052,636 B2 * | 11/2011 | Moll | A61B 17/062 | 600/114 |
| 8,157,834 B2 * | 4/2012 | Conlon | A61B 17/29 | 606/205 |
| 8,167,798 B2 * | 5/2012 | Sperling | A61B 17/02 | 600/219 |
| 8,257,303 B2 * | 9/2012 | Moll | A61B 17/062 | 600/114 |
| 8,262,605 B2 * | 9/2012 | Copa | A61M 5/3007 | 600/104 |
| 8,262,655 B2 * | 9/2012 | Ghabrial | A61B 18/1445 | 606/51 |
| 8,353,487 B2 * | 1/2013 | Trusty | A61B 1/00149 | 248/121 |
| 8,361,066 B2 * | 1/2013 | Long | A61B 18/1206 | 606/32 |
| 8,657,740 B2 * | 2/2014 | Bonadio | A61B 17/3423 | 600/201 |
| 2002/0074004 A1 * | 6/2002 | Boyd | A61B 17/00234 | 128/898 |
| 2005/0049623 A1 * | 3/2005 | Moore | A61B 17/1604 | 606/170 |
| 2005/0143774 A1 * | 6/2005 | Polo | A61B 17/0469 | 606/205 |
| 2005/0165415 A1 * | 7/2005 | Wales | A61B 17/07207 | 606/139 |
| 2005/0250988 A1 * | 11/2005 | Ewers | A61B 1/0014 | 600/102 |
| 2006/0100644 A1 * | 5/2006 | Viola | A61B 17/07207 | 606/142 |
| 2006/0148903 A1 * | 7/2006 | Burch | A61K 9/0014 | 514/627 |
| 2006/0178560 A1 * | 8/2006 | Saadat | A61B 1/0055 | 600/114 |
| 2006/0184188 A1 * | 8/2006 | Li | A61B 17/1617 | 606/180 |
| 2006/0210605 A1 * | 9/2006 | Chang | A61B 17/24 | 424/434 |
| 2006/0235379 A1 * | 10/2006 | McClurken | A61B 18/1445 | 606/45 |
| 2006/0270901 A1 * | 11/2006 | Bern | A61B 1/0016 | 600/114 |
| 2006/0270902 A1 * | 11/2006 | Igarashi | A61B 17/3403 | 600/114 |
| 2006/0287577 A1 * | 12/2006 | Wendlandt | A61B 1/00156 | 600/146 |
| 2007/0021760 A1 * | 1/2007 | Kelleher | A61B 17/0469 | 606/153 |
| 2007/0043338 A1 * | 2/2007 | Moll | A61B 19/2203 | 606/1 |
| 2007/0185376 A1 * | 8/2007 | Wilson | A61B 17/02 | 600/102 |
| 2007/0203550 A1 * | 8/2007 | Perez | A61N 5/0603 | 607/86 |
| 2007/0213743 A1 * | 9/2007 | McGuckin, Jr. | A61B 17/00234 | 606/139 |
| 2007/0255109 A1 * | 11/2007 | Stein | A61B 1/00087 | 600/214 |
| 2007/0299387 A1 * | 12/2007 | Williams | A61B 1/00052 | 604/22 |
| 2008/0009854 A1 * | 1/2008 | Yates | A61B 18/14 | 606/42 |
| 2008/0058835 A1 * | 3/2008 | Farritor | A61B 1/00158 | 606/130 |
| 2008/0064921 A1 * | 3/2008 | Larkin | A61B 1/00087 | 600/104 |
| 2008/0188868 A1 * | 8/2008 | Weitzner | A61B 1/0014 | 606/130 |
| 2008/0188890 A1 * | 8/2008 | Weitzner | A61B 1/0014 | 606/205 |
| 2008/0221391 A1 * | 9/2008 | Weitzner | A61B 1/0014 | 600/118 |
| 2008/0243176 A1 * | 10/2008 | Weitzner | A61B 1/0014 | 606/206 |
| 2008/0255607 A1 * | 10/2008 | Zemlok | A61B 17/07207 | 600/127 |
| 2008/0262293 A1 * | 10/2008 | Murakami | A61B 1/0052 | 600/102 |
| 2008/0262302 A1 * | 10/2008 | Azarbarzin | A61B 1/00052 | 600/114 |
| 2008/0272172 A1 * | 11/2008 | Zemlok | A61B 17/07207 | 227/175.1 |
| 2009/0054805 A1 * | 2/2009 | Boyle, Jr. | A61B 10/0266 | 600/564 |
| 2009/0081129 A1 * | 3/2009 | Neff | C07D 487/04 | 424/9.6 |
| 2009/0112254 A1 * | 4/2009 | Yates | A61B 18/14 | 606/207 |
| 2009/0143639 A1 * | 6/2009 | Stark | A61B 1/018 | 600/102 |
| 2010/0137681 A1 * | 6/2010 | Ewers | A61B 17/00234 | 600/102 |
| 2010/0234687 A1 * | 9/2010 | Azarbarzin | A61B 17/29 | 600/201 |
| 2010/0286473 A1 * | 11/2010 | Roberts | A61B 17/00234 | 600/37 |
| 2010/0331883 A1 * | 12/2010 | Schmitz | A61B 10/0275 | 606/249 |
| 2011/0060183 A1 * | 3/2011 | Castro | A61B 17/3421 | 600/104 |
| 2011/0230723 A1 * | 9/2011 | Castro | A61B 17/3421 | 600/205 |
| 2011/0238083 A1 * | 9/2011 | Moll | A61B 17/062 | 606/130 |
| 2011/0282157 A1 * | 11/2011 | Hart | A61B 17/0293 | 600/208 |
| 2012/0004502 A1 * | 1/2012 | Weitzner | A61B 1/0014 | 600/102 |
| 2012/0065467 A1 * | 3/2012 | Moll | A61B 17/062 | 600/106 |
| 2012/0095451 A1 * | 4/2012 | Hegeman | A61B 1/0055 | 606/1 |
| 2012/0101496 A1 * | 4/2012 | McClurken | A61B 17/32 | 606/41 |
| 2012/0209174 A1 * | 8/2012 | Moll | A61B 17/062 | 604/95.01 |
| 2012/0209297 A1 * | 8/2012 | Jugenheimer | A61B 17/10 | 606/142 |
| 2012/0215072 A1 * | 8/2012 | Sperling | A61B 17/02 | 600/219 |
| 2012/0259263 A1 * | 10/2012 | Celermajer | A61B 18/1492 | 604/8 |
| 2012/0283518 A1 * | 11/2012 | Hart | A61B 17/3498 | 600/207 |
| 2012/0310167 A1 * | 12/2012 | Kraus | A61B 17/3462 | 604/167.03 |
| 2012/0316574 A1 * | 12/2012 | Coleman | A61B 17/00234 | 606/130 |
| 2014/0343367 A1 * | 11/2014 | Lunsford | A61B 1/3137 | 600/208 |
| 2015/0018710 A1 * | 1/2015 | Furlong | A61B 17/320016 | 600/563 |

\* cited by examiner

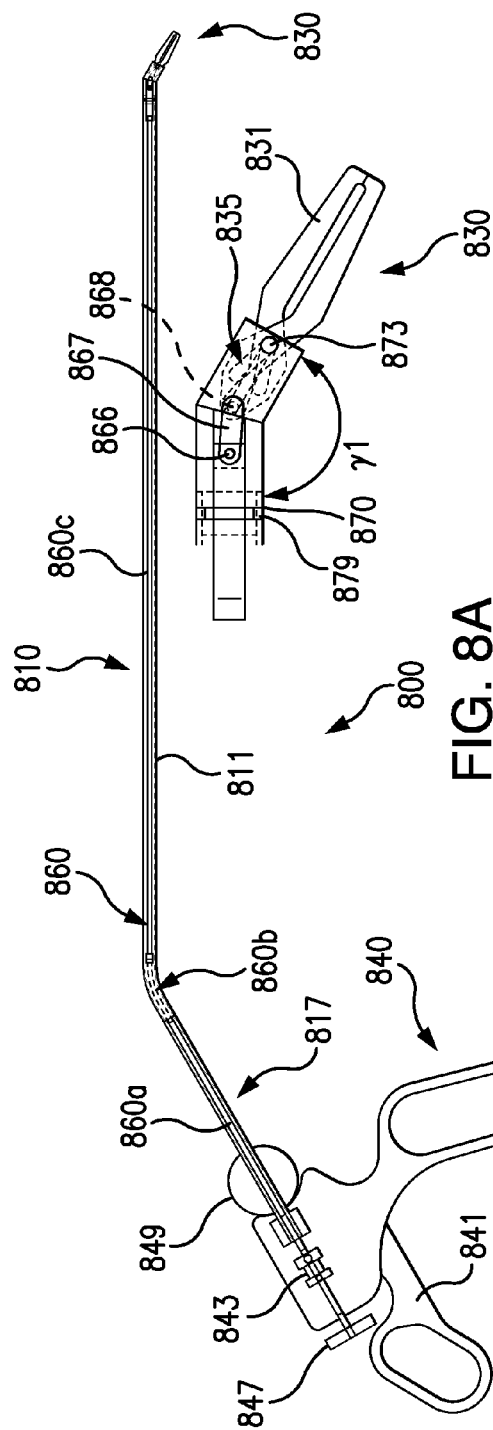
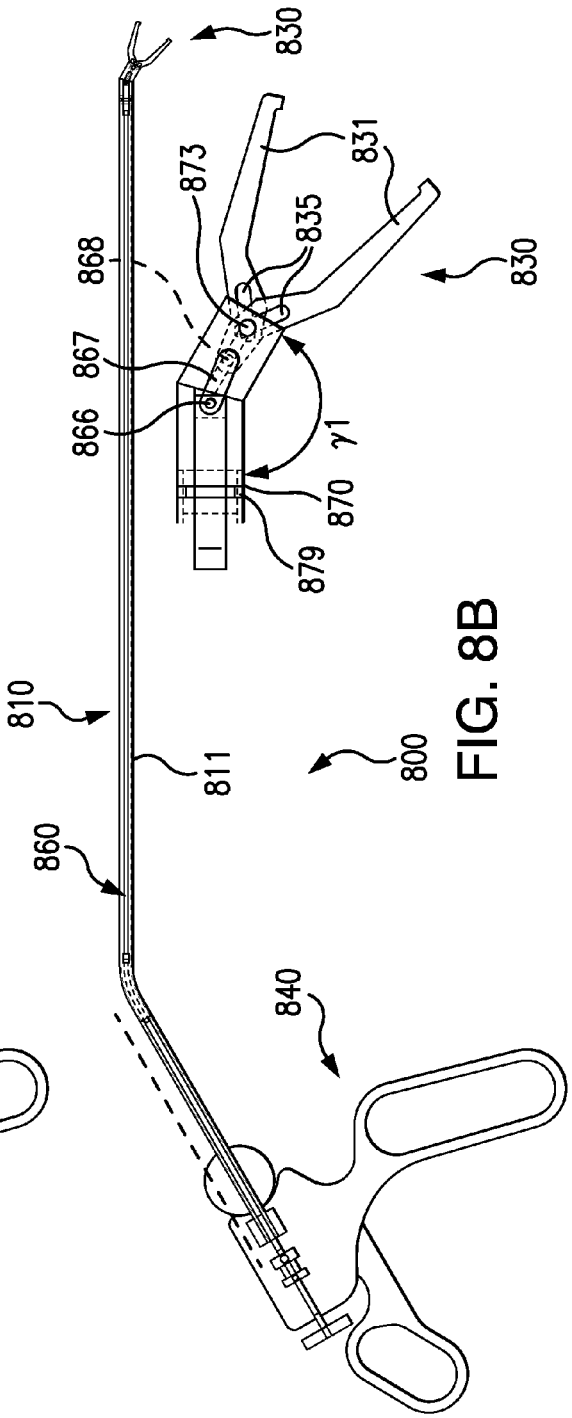

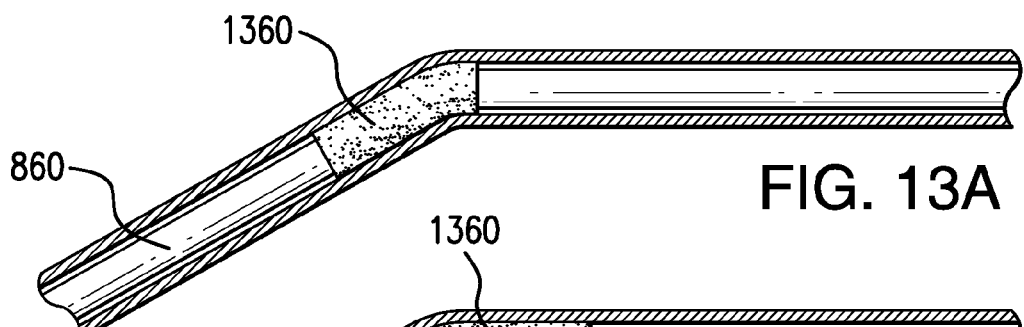
FIG. 13A
FIG. 13B
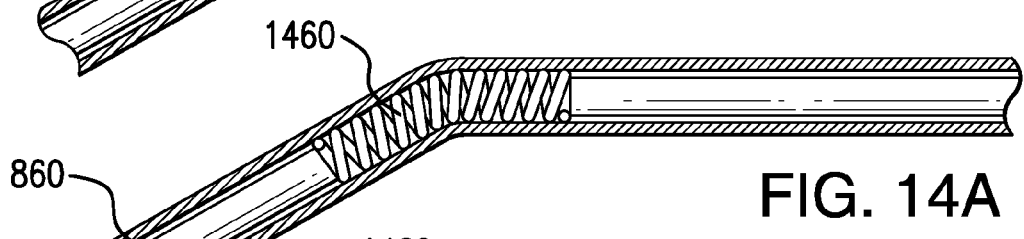
FIG. 14A
FIG. 14B
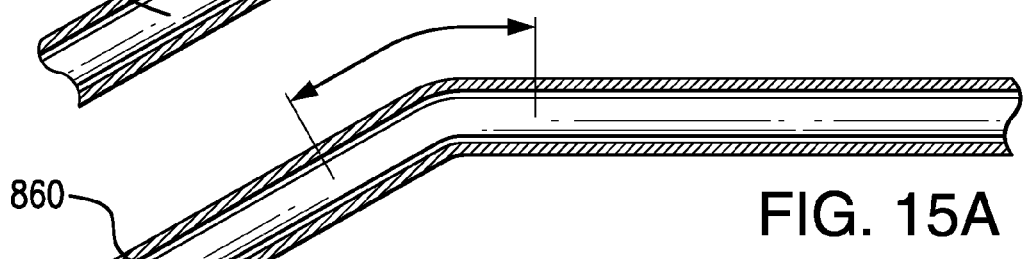
FIG. 15A
FIG. 15B

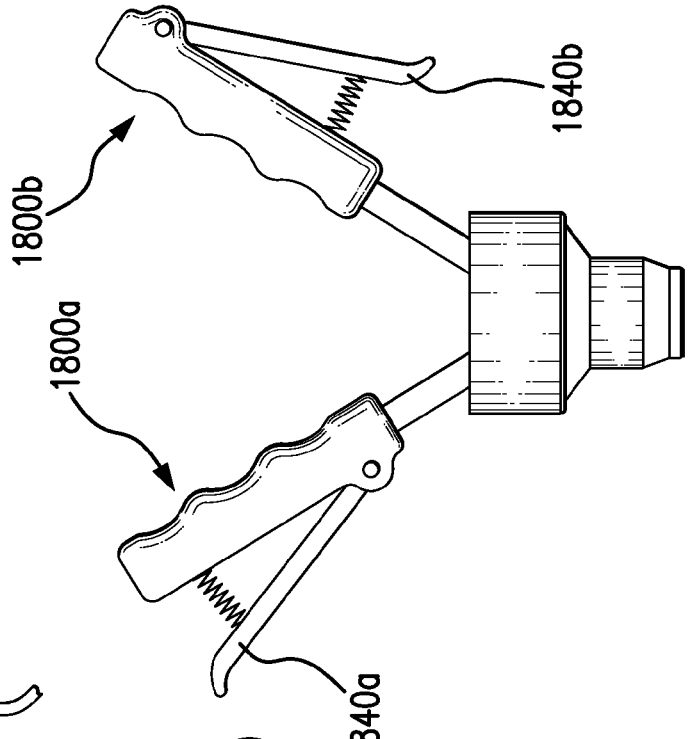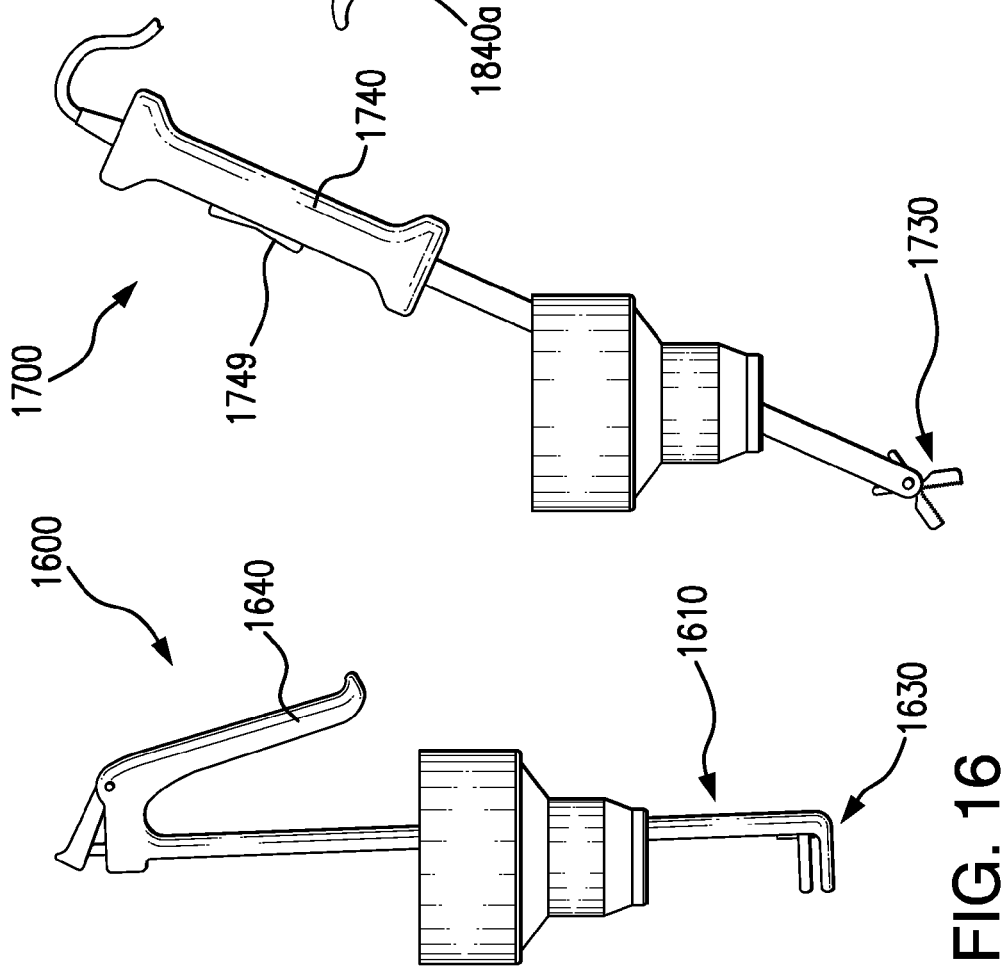
FIG. 18
FIG. 17
FIG. 16

SURGICAL INSTRUMENTS WITH IMPROVED DEXTERITY FOR USE IN MINIMALLY INVASIVE SURGICAL PROCEDURES

CROSS-REFERENCE TO RELATED APPLICATIONS

This application is a divisional of U.S. patent application Ser. No. 12/789,643 filed May 28, 2010 which claims the benefit of priority to International Patent Application No. PCT/US2008/085081, which in turn claims the benefit of priority to U.S. Patent Application Ser. No. 60/991,150 filed Nov. 29, 2007, U.S. Patent Application Ser. No. 61/053,038 filed May 14, 2008, U.S. Patent Application Ser. No. 61/091,335 filed Aug. 22, 2008, and U.S. Patent Application Ser. No. 61/104,532 filed Oct. 10, 2008. Each of the aforementioned patent applications is incorporated herein by reference in its entirety.

FIELD OF THE INVENTION

The present invention relates to instruments for use in minimally invasive surgical procedures and methods relating thereto. Particularly, the present invention is directed to instruments having an elongated shaft, an actuator at a proximal end and an effector at a distal end thereof, and to surgical methods utilizing such devices.

BACKGROUND

A variety of surgical devices are known in the art to aid in performing surgical procedures. Typical surgical devices of this kind are fully rigid, including an elongate shaft rigidly affixed to a handle at a proximal end thereof. Such handles and any actuator thereon are typically configured with a pistol-type grip, as in the case of a surgical stapler, or with a scissor handle, as in the case of many other devices, such as some graspers, for example. The handles are typically arranged at the proximal end of the device, in-line with the longitudinal axis of the device or deviated therefrom by an acute angle. Examples of such devices are set forth, for example, in U.S. Pat. No. 7,258,262 to Mastri et al, U.S. Pat. No. 5,820,009 to Melling et al., U.S. Pat. No. 5,462,558 to Kolsea et al. and U.S. Pat. No. 5,728,121 to Bimbo et al., each of which documents is hereby incorporated by reference in its entirety.

Applicant recognizes, however, that such typical instruments pose difficulties when used in conjunction with other instruments in a small space, such as during laparoscopic procedures, and particularly during such procedures through a single or limited number of access ports. Under such conditions, typical devices in the art suffer from interference between handles and/or effector ends of other such devices.

Moreover, during laparoscopic surgical procedures, the movement of the surgical instrument tip is typically restricted to a region relatively proximal to an axis of a surgical access port, such as that of a surgical cannula. Typically, this disadvantage is mitigated through use of multiple access ports distributed across a patient's abdomen.

Increasingly, techniques are being developed for performing minimally invasive surgical procedures through a single access port. With the advent of such surgeries, it has become necessary to insert multiple instruments through a single access port. Accordingly, the relative motion of, and distance between instrument tips are restricted by the inner diameter of the access port. With traditional instruments, instrument effector ends can interfere with one another while also not being capable of reaching a wide range of areas, or of approaching such areas from different angles.

Additionally, as mentioned above, in such procedures with traditional laparoscopic hand instruments, it becomes difficult to manipulate the handles at the proximal end (user end) thereof, due to crowding due from mutual interference between multiple instrument handles in a relatively small area.

Certain surgical access devices or access "ports" have been developed which have particular advantages with single-incision surgeries, including those devices described in U.S. Pat. Nos. 7,182,752, 7,338,473, and 7,285,112, U.S. Patent Application Publication Number US 2007/0088275 and PCT Publication Number WO2008/077080, which documents are fully incorporated herein by reference. The surgical access devices described in these documents utilize a non-mechanical pressure sealing capability to prevent depressurization of the abdominal cavity during laparoscopic abdominal surgeries. The absence of reliance upon purely mechanical seals, as is common in traditional surgical access devices, allows for the simultaneous use of multiple instruments through a single access device inserted through a single incision, while maintaining a pressurized abdominal cavity (pneumoperitoneum). Traditional mechanically-sealed surgical access devices suffer from various drawbacks when multiple instruments are inserted, or even when a single instrument is manipulated off axis, usually resulting in loss of pneumoperitoneum and/or torn seals or other problems.

Accordingly, Applicant recognizes that there remains a need in the art for devices that are capable of reduced interference with other instruments, which facilitate simultaneous use of multiple instruments in a confined space.

Furthermore, one objective of the present invention, is to provide instruments that are particularly suited for use in single-incision surgeries, which allow for greater freedom of movement at the proximal end, reducing crowding and allowing the surgeon an ergonomically advantageous position. Another objective of the present invention is to provide a surgeon with a greater range of motion between instrument tips during laparoscopic surgery, particularly in single-port surgeries. Among other advantages, instruments in accordance with the invention will enhance a surgeon's dexterity, reduce fatigue and improve accuracy during laparoscopic surgical procedures, particularly during single-incision laparoscopic surgical procedures.

SUMMARY

The purpose and advantages of the present invention will be set forth in and apparent from the description that follows. To achieve these and other advantages and in accordance with the purpose of the invention, as embodied, the invention includes a surgical instrument adapted and configured for use in minimally invasive surgical procedures that includes a longitudinal shaft, a distal end effector and a proximal handle. The longitudinal shaft has proximal and distal end portions, and defines a longitudinal axis of the surgical instrument. The distal end effector is connected to the distal end portion of the shaft, and is adapted and configured for performing a surgical task. For example, such end effector can be a shear, a stapler or of another type. The proximal handle portion is connected to the proximal end portion of the longitudinal shaft and has an actuatable portion operably connected to the end effector to result in movement of the end effector when actuated.

If desired, the distal end portion of the shaft can be laterally offset from the longitudinal axis of the shaft. Additionally or alternatively, the distal end portion of the shaft can have an arcuate portion that deviates from the longitudinal axis of the shaft. The arcuate portion can be formed so as to curve in a plane that is substantially orthogonal, with respect to the longitudinal axis of the shaft, to a plane in which the lateral jog is formed. Alternatively, the arcuate portion can be formed so as to curve in a plane that is substantially parallel, with respect to the longitudinal axis of the shaft, to a plane in which the lateral jog is formed.

Additionally or alternatively, the proximally arranged handle portion of the surgical instrument can be arranged such that it extends away from the longitudinal axis of the shaft of the surgical instrument.

In accordance with one aspect of the invention, a method of performing a laparoscopic cholecystectomy is provided. The method includes: inserting a single access port through the abdominal wall of a patient, introducing a scope through the access port, inserting a surgical grasper through the access port, lifting the gall bladder with the surgical grasper, inserting a dissector through the access port, dissecting the cystic duct and artery with the dissector, inserting a clip applier and surgical scissor through the access port, terminating the cystic duct and artery with the clip applier, cutting the cystic duct and artery with a surgical scissor, inserting an energy device through the access port, dissecting the gall bladder from the liver bed with the energy device, introducing a specimen bag through the access port, removing the gallbladder from the abdominal cavity with the specimen bag, removing the access port, and closing the incision with a suitable closure.

In accordance with a further aspect of the invention, a surgical instrument for laparoscopic procedures includes a handle, an elongated shaft extending therefrom, and an effector at a distal end of the shaft. The shaft includes one or more bends or curves formed therein. An actuating member extends from the handle through the elongated shaft, and includes a plurality of axially-connected shaft portions including rigid and flexible portions. The effector is provided on a distal end of the elongated shaft, and is operatively connected to the actuating member for performing a surgical task.

The one or more bends or curves can include a bend in a proximal portion of the shaft. In accordance with the invention, the bend can be between about 10 and 170 degrees. In accordance with a preferred aspect, the bend is between about and 20 and 60 degrees. The one or more bends or curves can include an arcuate curve in the distal portion of the shaft.

The one or more bends or curves can be provided in the shaft such that the position of the handle portion, when the instrument is in a working position, inserted through a surgical access device in a laparoscopic procedure, for example, is such that it approximates the position of a handle of a surgical instrument used in an open surgical procedure.

The one or more bends or curves can be provided such that when a plurality of instruments are inserted through a single access device, a portion of the shaft of the surgical instruments passing through the surgical access device are mutually substantially parallel, and a proximal end portion of the surgical instruments extend away from a longitudinal axis of the respective surgical instrument.

If desired, the handle portion can be rotatably connected to the proximal end portion of the shaft, and the end effector can be rotatably connected to the distal end portion of the shaft. In this case, the handle portion and the end effector are mutually connected such that relative rotation of the handle portion with respect to the shaft causes relative rotation of the end effector with respect to the shaft. Accordingly, a flexible connecting member, such as a cable for example, is provided in the shaft to transfer a rotational force from the handle portion to the end effector.

It is to be understood that both the foregoing general description and the following detailed description are exemplary and are intended to provide a non-limiting explanation of the invention.

BRIEF DESCRIPTION OF THE DRAWINGS

The accompanying drawings, which are incorporated in and constitute part of this specification, are included to illustrate and provide a further understanding of the method and system of the invention. Together with the description, the drawings serve to explain the principles of the invention, wherein:

FIGS. 8A and 8B illustrate side and isometric views of a surgical instrument in accordance with the invention, in open and closed positions, respectively;

FIG. 13A is a cross-sectional view of a further example shaft construction for surgical instruments in accordance with the invention;

FIG. 13B is a cross-sectional view of the shaft construction of FIG. 13A showing a flexible portion and a respective actuating element transmitting forces through a bend in the shaft;

FIG. 14A is a cross-sectional view of a further example shaft construction for surgical instruments in accordance with the invention;

FIG. 14B is a cross-sectional view of the shaft construction of FIG. 14A showing a flexible portion and a respective actuating element transmitting forces through a bend in the shaft;

FIG. 15A is a cross-sectional view of a further example shaft construction for surgical instruments in accordance with the invention;

FIG. 15B is a cross-sectional view of the shaft construction of FIG. 15A showing a respective actuating element transmitting forces through a bend in the shaft; and FIGS. 16-18 are side views of surgical instruments having alternative handle and effector end constructions, in accordance with the invention.

DETAILED DESCRIPTION

Reference will now be made in detail to the presently preferred embodiments of the invention, examples of which are illustrated in the accompanying drawings.

The devices and methods presented herein may be used for minimally invasive surgical procedures, but may be used for more conventional surgical procedures. The present invention is particularly suited for use in minimally invasive surgical procedures performed through a single or limited number of access ports, when multiple instruments are required at the same time.

Figure 1:
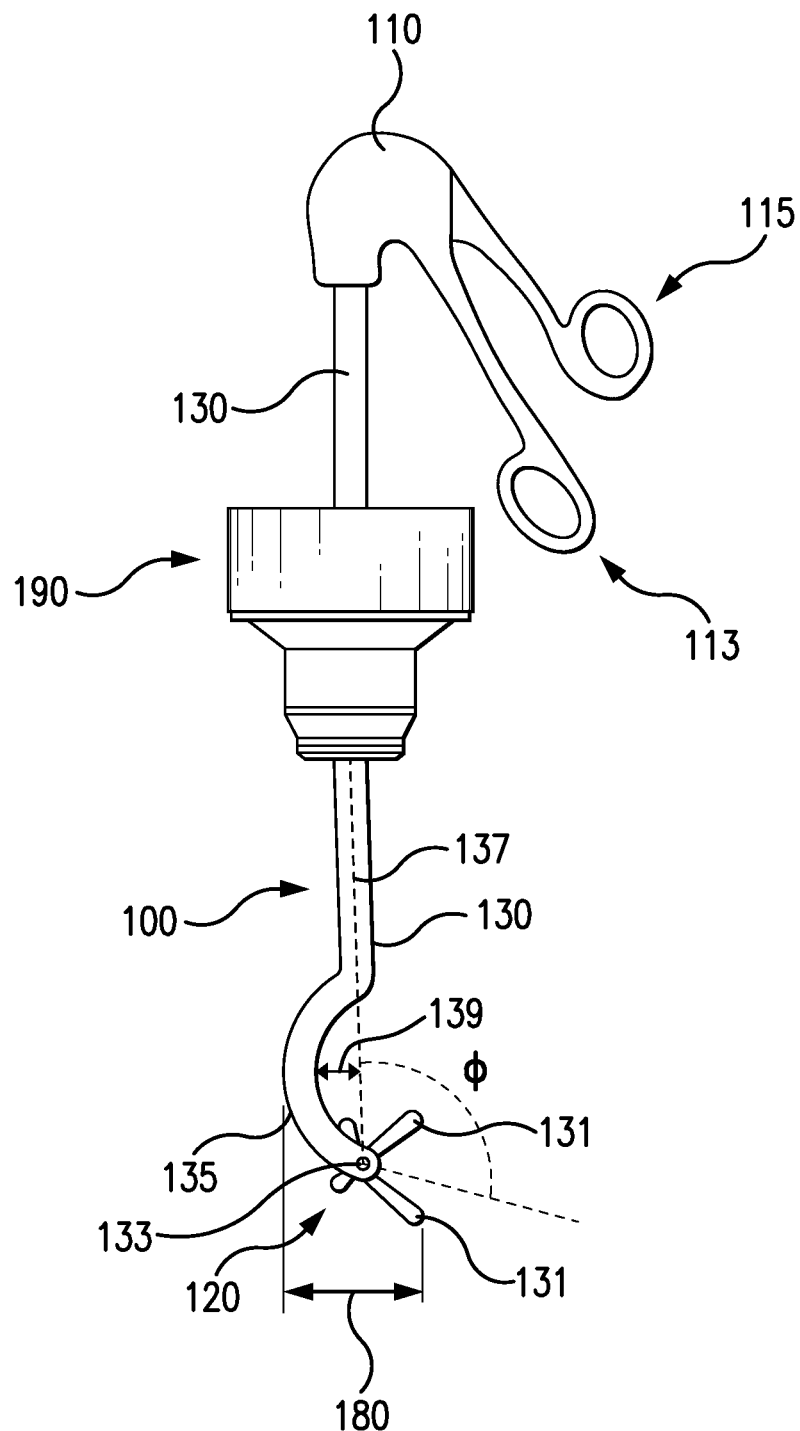
FIG. 1 is a side view of an example surgical hand instrument constructed in accordance with one aspect of the invention, shown inserted through a surgical access port.
Figure 2:
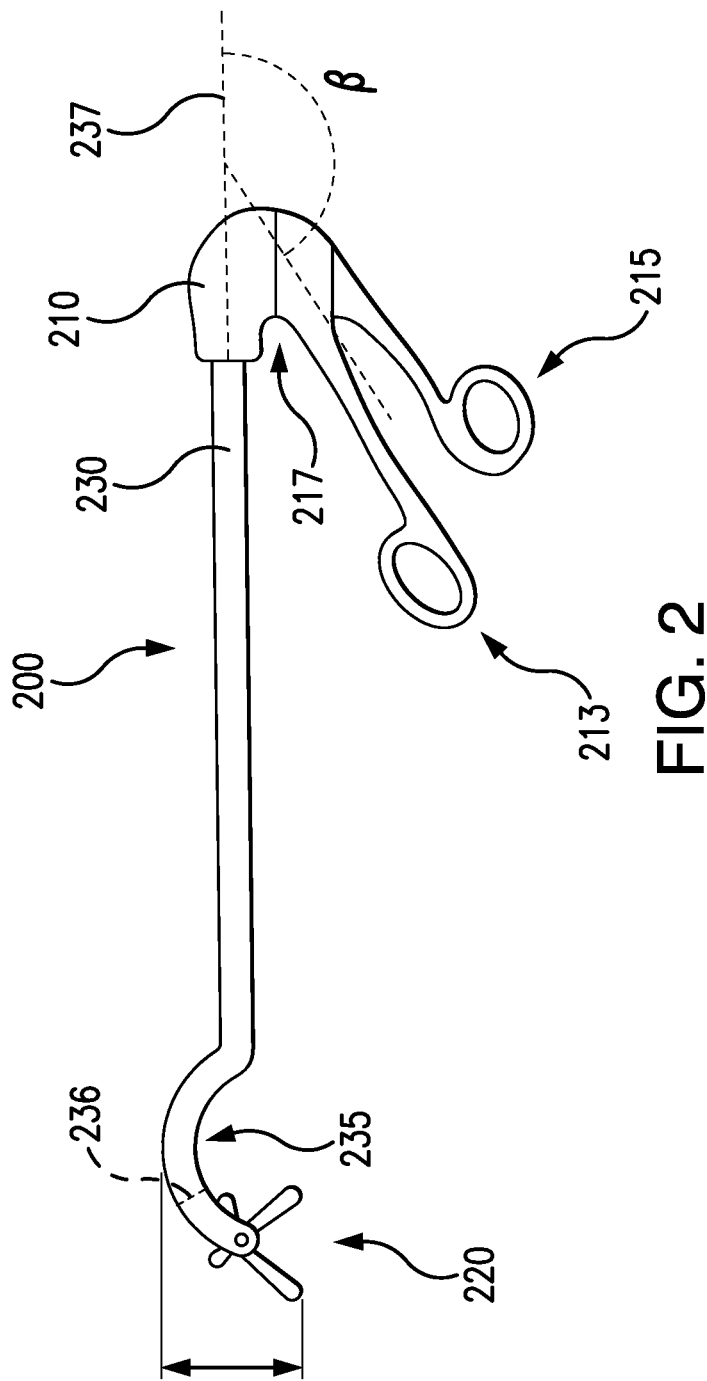
FIG. 2 is a side view of the surgical hand instrument of FIG. 1, with the surgical access port absent.

For the purposes of explanation and illustration, and not limitation, a side view of an exemplary embodiment of the surgical hand instrument in accordance with the invention is shown in FIG. 1, where the surgical instrument is inserted through a surgical access port 190. The surgical access port 190 can be any suitable type, but in accordance with one aspect of the invention preferably includes a fluidic seal, such as those described in U.S. Pat. Nos. 6,030,402, 6,056,766, 6,447,527, 7,182,752, 7,285,112 and U.S. Patent Publication No. 2007/0088275, which documents are incorporated herein by reference in their entirety. The surgical hand instrument is designated generally by reference character 100. FIG. 2 illustrates a similar surgical hand instrument 200 with the surgical access port 190 absent.

As shown in FIGS. 1 and 2, the surgical hand instruments 100, 200 are each adapted and configured for use in minimally invasive surgical procedures and each include a longitudinal shaft 130, 230, a distal end effector 120, 220 and a proximal handle 110, 210.

The longitudinal shaft 130 has proximal and distal end portions and defines a longitudinal axis 137 of the surgical instrument 100. The distal end effector 120 is connected to the distal end portion of the shaft 130, and is adapted and configured for performing a surgical task. For example, such end effector 120 can be a shear as illustrated in FIGS. 1 and 2, a stapler or any effector desired. Effector 120 includes a pair of tool members 131 mounted for relative motion about a common pivot point 133 on the distal end portion 135 of the shaft 130. The proximal handle portion 110 is connected to the proximal end portion of the longitudinal shaft 130 and has a stationary portion 113 and an actuatable portion 115 operably connected to the end effector 120 to result in movement of the end effector 120 when actuated by a surgeon. If desired, the distal end portion 135 of the shaft 130 can be laterally offset from the longitudinal axis of the shaft.

As illustrated in FIG. 1, the distal end portion of the shaft 130 is offset by a distance 139 from the longitudinal axis 137. As illustrated, the distal end portion 135 of the shaft 130 is arcuate in shape, but can be more angularly configured, as with straight sections if necessary. Naturally, the distal end portion 135 need not be curved at all, and can be straight and in-line with the longitudinal axis 137.

Moreover, in the illustrated embodiment, the distal end portion 135 of the shaft 130 curves back toward the longitudinal axis 137, leaving the end effector 120 essentially where it would have been if no deviation were present in the shaft 130. Alternatively, if so-desired, the end effector 120 can remain laterally offset from the longitudinal axis 137, rather than returning to a laterally central position.

Further, as illustrated, the distal end of the shaft end portion 135 and the end effector 120 terminate at an angle of φ (phi) with respect to the longitudinal axis 137. This angle can range from an acute angle of about 0 degrees to an angle of about 180 degrees and can be at any one-degree increment therebetween, as desired for the particular application. As illustrated in FIG. 1, the angle φ (phi) is about 100 degrees. If so desired, the end effector 120 and/or the shaft distal end portion 135 can be adjustable such that the angle φ (phi) is adjustable. Although the shaft 130 is preferably substantially rigid, the shaft may instead be fully or partially flexible, such as at its distal end portion 135, to allow for adjustability in different situations Moreover, the overall width 180, due to the offset 139 and the angle of the end effector 120 is preferably selected such that it is no greater than the largest diameter of the access port being used. Naturally, when multiple such instruments are inserted, the space available for insertion of the end effector through the access port must be considered. In such an instance, a flexible shaft portion can allow for adjustment of the end effector once inserted through the access port. Devices in accordance with the invention can advantageously be used with access ports having major and minor axes, such as an elliptically-shaped access port. The extra width available can allow for instruments constructed in accordance with the invention to pass more easily therethrough.

With reference to FIG. 2, although applicable to any embodiment set forth herein, the proximal handle portion 210 (as well as handle portion 110 of the embodiment of FIG. 1), are oriented at an angle β (beta) with respect to the longitudinal axis 237 of the surgical hand instrument 200. As illustrated, this angle β (beta) is obtuse. The angle can be any angle desired between about 0 and 180 degrees, but is preferably between about 90 degrees and 145 degrees. In a preferred embodiment, the angle is about 135 degrees. Additionally, the proximal handle portion 210 can be configured such that the angle β (beta) is adjustable. Such adjustability may further reduce mutual interference between adjacent instruments, and can further improve ergonomics for the user, allowing the user to position the handles in the most comfortable position for the procedure or specific situation.

This offset of the handle portion 110, 210 and/or end effectors 120, 220, allows for reduced interference between instruments during use, particularly when they are concurrently inserted through a single surgical access port.

Additionally, as illustrated in the embodiment of FIG. 2, the stationary portion 213 and the actuatable portion 215 of the handle 210 can be rotatably attached to the remainder of the handle portion 210 by way of a joint element 217. This, in-turn, can be connected through the shaft 230 by way of any suitable element, such as a cable or other flexible member to impart rotational force from the handle 210 to the end effector 220. The end effector 220 can be, in-turn, rotatably attached to the distal end portion 235 of the shaft 230 by way of a joint 236, allowing relative rotation between the shaft 230 and the end effector 220. In either of the embodiments of FIG. 1 and FIG. 2, the end effector 220 can be actuated normally, by moving the actuatable portion 215 of the handle 210 relative to the stationary portion 213.

End effectors which may be used with devices constructed in accordance with the invention include but are not limited to clip appliers, staplers, morcellators, dissectors, shears, graspers, suturing devices, ligating loops, specimen retrievers, retractors, biopsy punches, probes, irrigation cannulas, scissors, forceps, needle holders, electrocautery devices, coagulating devices, and clamps. In accordance with any embodiment of the invention, the end effector and instrument can be configured such that the end effectors are interchangeable. That is, the end effectors can be removable and replaceable with the same or different type of end effector.

Although illustrated and described as being actuatable only by hand, devices in accordance with the invention can be modified so as to be used in conjunction with robotic surgical systems. In this case, the proximal handle portion (110, 210) is replaced with a suitable engaging and interface portion to adapt the surgical instruments described herein for use with such systems.

Devices constructed in accordance with the invention can facilitate various minimally invasive surgical procedures using a minimal number of access ports, including cholecystectomy, sleeve gastrectomy, nephrectomy, colon resection, hysterectomy, appendectomy, oophorectomy, or mass removal.

For example, a laparoscopic cholecystectomy, in accordance with one aspect of the invention, includes a first step of inserting a single access port through the umbilicus or in another location in the abdomen of the patient. As set forth above, the access port, in accordance with one aspect of the invention, includes a fluidic seal. Such access ports can be relatively large in size to accommodate multiple instruments, and be circular or non-circular in cross-section, including oval, for example. Diameters or axial dimensions, in accordance with one aspect, are in the range of about 12 mm to about 25 mm. Larger sizes allow for insertion of more and/or larger instruments, and facilitate tissue removal through the port.

Subsequently, a scope can be introduced through the access port, which may be a flexible endoscope or laparoscope, for example. All subsequent steps can be performed by inserting the appropriate instrument or instruments through the access port. In the case of a cholecystectomy, the gallbladder can be lifted with surgical grassers or another suitable instrument. The cystic duct and artery can then be dissected with a suitable instrument, such as a dissector. The cystic duct and artery can be terminated, for example, clipped with a clip applier and cut with a suitable instrument, such as a surgical scissor.

The gall bladder can then be removed, and is dissected from the liver bed prior to removal with a suitable instrument, such as an energy device, which can be a cautery device or harmonic device, for example. Subsequently, a specimen bag can be introduced to remove the gallbladder from the abdominal cavity. Upon completion of the procedure, the access port can be removed, and the incision can be closed with sutures or by another suitable closure.

A sleeve gastrectomy can be performed in accordance with the invention including the steps of inserting the required number of access ports, but preferably only a single port, in the abdomen of a patient, such as through the umbilicus as set forth above. The method can further include introducing a scope, and transecting small gastric vessels with a grasper and energy source, for example. An energy source can include ultrasonic, Ligasure™ (Manufactured by ValleyLab, a division of Tyco Healthcare Group LP) or bipolar energy sources, for example. Further steps included in accordance with this aspect are retracting the stomach laterally, sizing a sleeve such as by inserting a bougie via the mouth, transecting the stomach, such as with a surgical stapler, removing a specimen or excess tissue, with graspers, for example, and finally removing the access port and closing the incision made to insert the access port.

A nephrectomy can be performed in accordance with the invention, including the steps of inserting a port and inserting a scope therethrough, as set forth above, dissecting and exposing the kidney, such as with dissectors, scissors and/or an energy source, ligating and transecting the ureter, such as with clips and scissors, and transecting renal vessels, such as with a surgical stapler or other suitable instrument. The method further includes removing the kidney such as with a specimen bag and/or through use of a morcellator. The procedure is completed by removing the access port and closing the incision made therefor, with sutures or other suitable closure.

A colon resection performed in accordance with one aspect of the invention includes the steps of inserting a port and inserting a scope therethrough, as set forth above, mobilizing the colon with a suitable instrument such as graspers, scissors, dissectors and/or an energy source, for example. The method can further include ligating the blood supply with a stapler and/or an energy source, for example, and transecting and removing the desired portion of the colon using a surgical stapler and a specimen bag, for example. Next, anastomosis can be performed using a surgical stapler, which can be an EEA stapler, and then the access port can be removed and the incision can be closed.

A laparoscopic hysterectomy can be performed in accordance with one aspect of the invention in the following steps: First, a single port is inserted into the abdominal cavity, such as through the umbilicus, as set forth above, followed by insertion of a scope therethrough. Next, the uterus is mobilized and the blood supply thereto is ligated and transected, using a grasper, energy source and/or surgical stapler, for example. Subsequently, the uterus can be removed vaginally, or alternatively can be removed through the access port. In the latter instance, a morcellator is preferably utilized to facilitate removal. Finally, the access port is removed, and the incision is closed.

In accordance with another aspect of the invention, an appendectomy can be performed laparoscopically, including the steps of inserting an access port and scope into the abdominal cavity, as set forth above, then grasping and exposing the appendix with a suitable instrument, such as surgical graspers. Subsequently, the mesoappendix is ligated, such as with a surgical stapler or energy source, the appendix is transected with a suitable instrument, such as a surgical stapler, the appendix is removed with a specimen bag, and the port is removed and the incision closed with sutures or other suitable closure.

An oophorectomy or mass removal can be accomplished laparoscopically in accordance with the invention, including the steps of inserting a port and scope as set forth above, exposing the ovary or mass with a suitable instrument, such as a surgical grasper, mobilizing the ovary/mass with dissectors, scissors or other suitable instrument, and ligating and transecting the ovary/mass with a suitable instrument, such as an energy source or surgical stapler.

In accordance with the invention, any of the foregoing methods can include more or fewer steps, and can include steps or utilize instruments that vary from those specifically set forth herein.

Additionally, in accordance with a preferred aspect of the invention, the abdominal cavity is insufflated during the procedures set forth above. Naturally, this can be accomplished in a conventional manner, such as with a veress needle. Alternatively, the access port can be adapted and configured to provide insufflation to the abdominal cavity.

In accordance with further aspects of the invention, the shafts of laparoscopic instruments designed and constructed in accordance herewith are curved, bent or otherwise offset in one or more planes. In accordance with one aspect, for example, bends and/or curves are formed in orthogonal vertical and horizontal planes.

Figure 3A:
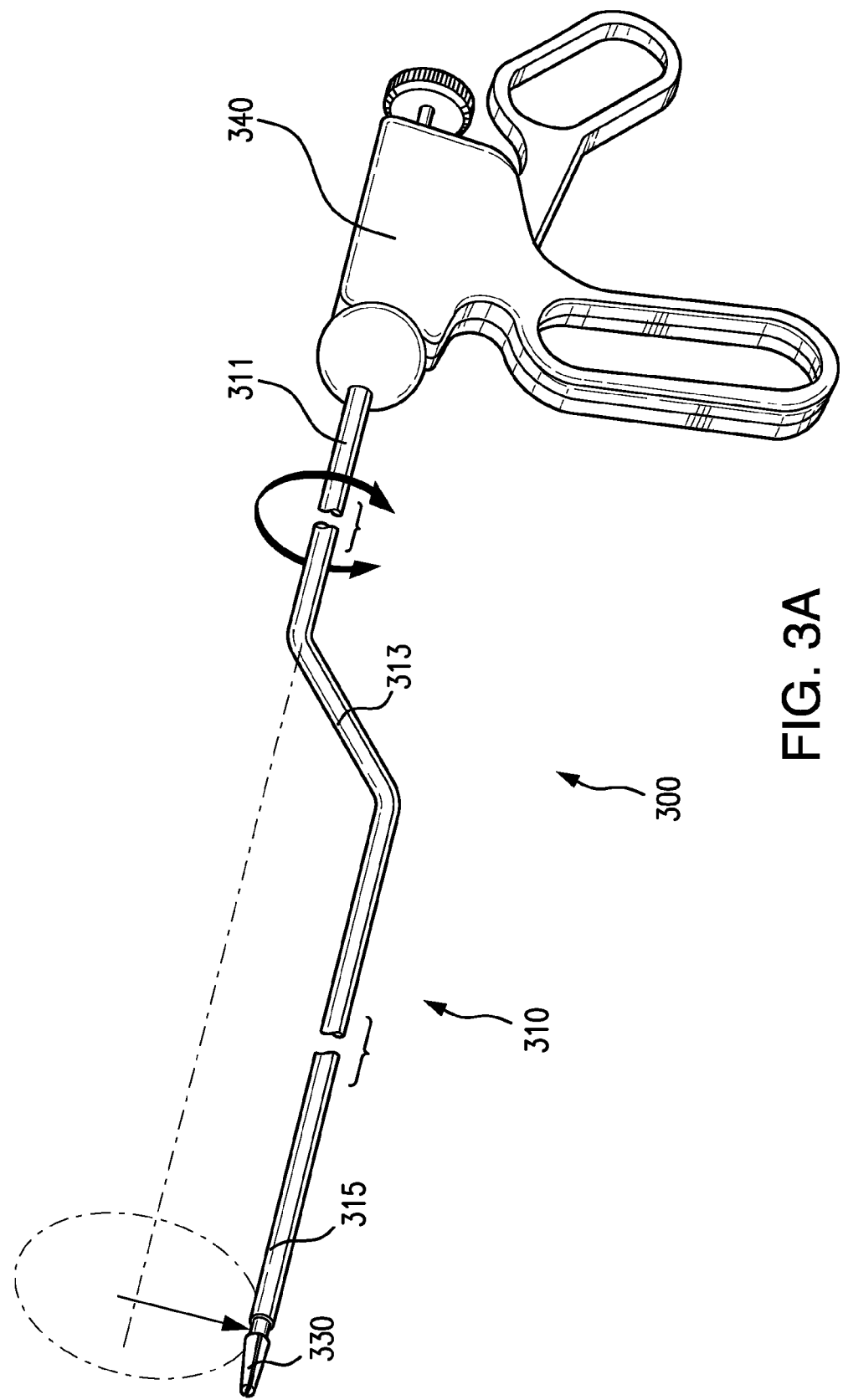
FIG. 3A is an isometric view of a surgical hand instrument in accordance with the invention, including a lateral jog formed in the shaft thereof.
Figure 3B:
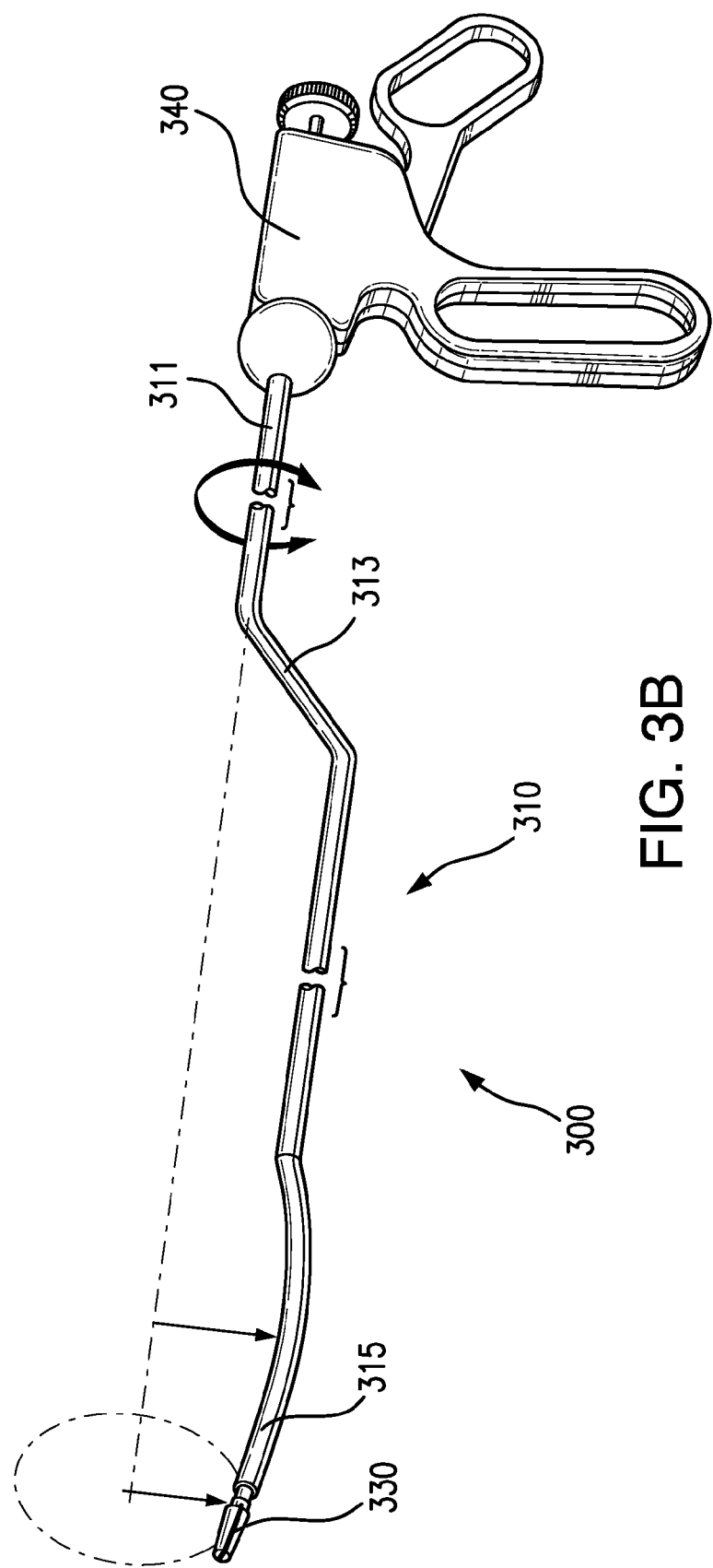
FIG. 3B is an isometric view of a surgical hand instrument in accordance with the invention, including a lateral jog formed in the shaft thereof and an arcuately curved distal shaft portion.

For example, and as illustrated in FIGS. 3A and 3B, in accordance with one aspect of the invention, a laparoscopic surgical instrument 300 has a main shaft 310, a proximal handle 340 and a distal effector end 330. The main shaft 310, as illustrated, has an integral jog formed therein such that the axis of the distal shaft portion 315 end is parallel to, but offset from the axis of the proximal end 311 of the instrument shaft. As illustrated particularly in FIG. 1, an angled shaft portion 313 between the proximal and distal shaft portions can be provided to offset the axis of the instrument. Accordingly, such a surgical instrument can be configured such that a rotation of the surgical instrument, or alternatively only the shaft thereof, results in a rotational and translational displacement of the effector end. Such instruments can be additionally configured so that rotation of another element, such as the handle 340 or a separate knob, for example, causes the effector end itself to rotate with respect to the shaft 310, further increasing dexterity.

Accordingly, in an embodiment such as that illustrated in FIGS. 3A and 3B, one or more instruments can be inserted through a surgical access port, and one or more of the shafts can be rotated, to move the distal (effector) end 330 of the instrument toward or away from the central axis of the access port, and accordingly toward or away from other surgical instruments being used at the same time. When rotated, the distance traveled is proportional to the product of the magnitude of the offset caused by the bent shaft portion 313 and the angle of rotation of the shaft. Accordingly, the proximal end of the instrument at the handle may be stationary, while the distal (effector) end 330 is displaced by a relatively large distance. Effector ends 330 for instruments in accordance with the invention can include any desired surgical tool, including but not limited to surgical graspers, dissectors scissors, scalpels, clamps and cautery devices.

In accordance with this aspect of the invention, the positioning of the jog in the shaft, causing lateral displacement of the distal portion 315 of the surgical instrument shaft 310 from the proximal portion 311 of the shaft 310, occurs in a location that is selected to be just distal to the end of the access port when in use. Accordingly, an instrument can advantageously be inserted through the access port, and then rotated out of the way, while another instrument is inserted, for example.

Additionally or alternatively, in accordance with the invention, and as illustrated in FIG. 1, the distal portion 315 of surgical instruments 300 in accordance with the invention can include an arcuate bend formed therein. The effector end 330, and/or the distal portion of the shaft 315 near the effector end 330, can optionally be bent or otherwise configured so as to provide further dexterity of the surgical instrument. In accordance with the invention, the lateral jog caused by a bent shaft portion 313 can be combined with the arcuate curve of the distal shaft portion 315, as shown in FIG. 3B, for example. As shown in FIG. 3B, the arcuate curve can be formed in a plane parallel to that in which the lateral jog is formed. Alternatively, the arcuate curve can be formed in a plane orthogonal to that in which the lateral jog is formed.

Figure 7:
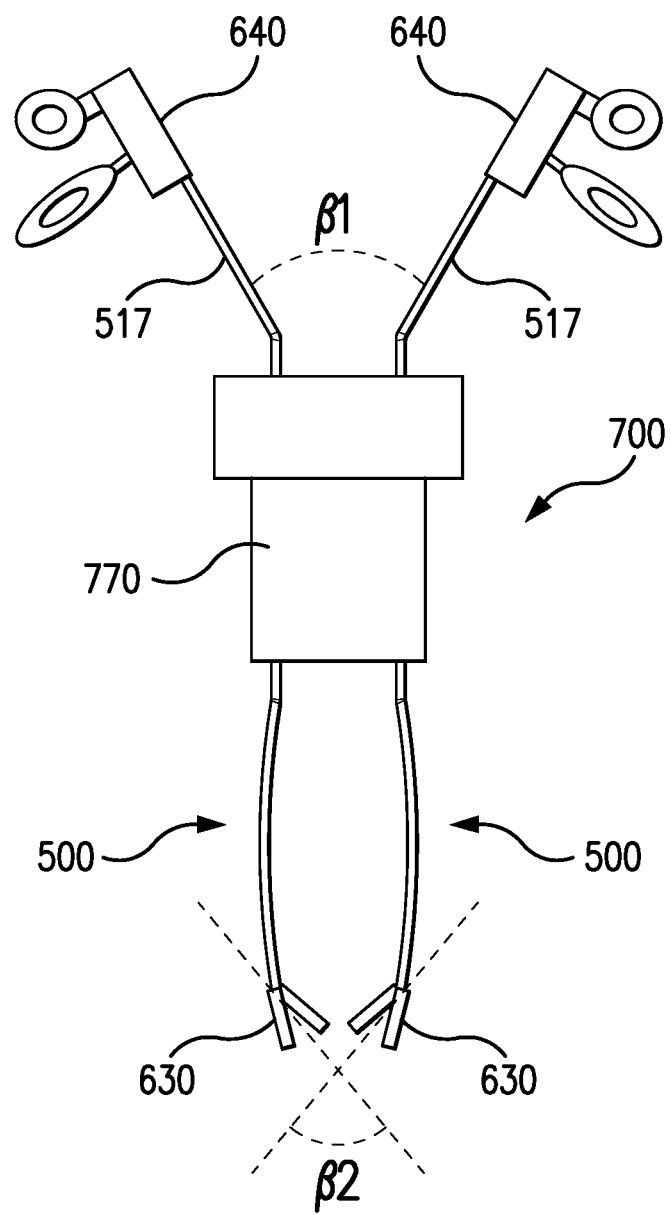
FIG. 7 is a side view of two surgical hand instruments shown in FIG. 6A, inserted through a surgical access device.

In such an arrangement, effector ends 330 of each of a pair of surgical instruments used in conjunction (as illustrated in FIG. 7, for example) inserted through an access port (e.g. access port 770) are able to triangulate with one another. If the shafts of the two instruments are rotated in opposite directions, the distal effector ends move apart by twice the distance of the individual offsets, proportional to the angle of rotation. Such ability is particularly advantageous in a scenario in which multiple surgical instruments are needed simultaneously in a surgical access port, which situation increasingly or completely inhibits relative cross-axis translation.

In accordance with a further aspect of the invention, a surgical instrument in accordance with the invention can be intentionally laterally restrained within a surgical cannula for the purpose of providing additional stability of the instrument, for example. In such an arrangement, the subject instruments can be configured and adapted to rotate, and optionally move inward and outward (axially), but inhibit lateral translation. However, with the configuration of the subject instruments, rotational movement results in translational movement, thereby allowing for additional stability without severely inhibiting dexterity.

In accordance with another aspect of the invention, and as illustrated in FIGS. 4-7, for example, there is illustrated a laparoscopic surgical instrument having a main shaft with a proximal angularly offset or "bent" portion 417, 517, a handle portion (e.g. 640) attached to the proximal angularly offset portion 417, 517 of the shaft 410, 510, an optional arcuately curved distal shaft portion 415, 515, and an effector (e.g. 630) operably connected to the distal end portion 415, 515 of the shaft 410, 510. The foregoing arrangement of an angularly offset handle, particularly in combination with an arcuately curved distal portion, allows for reduced interference between multiple instruments used at the same time.

Figure 4:
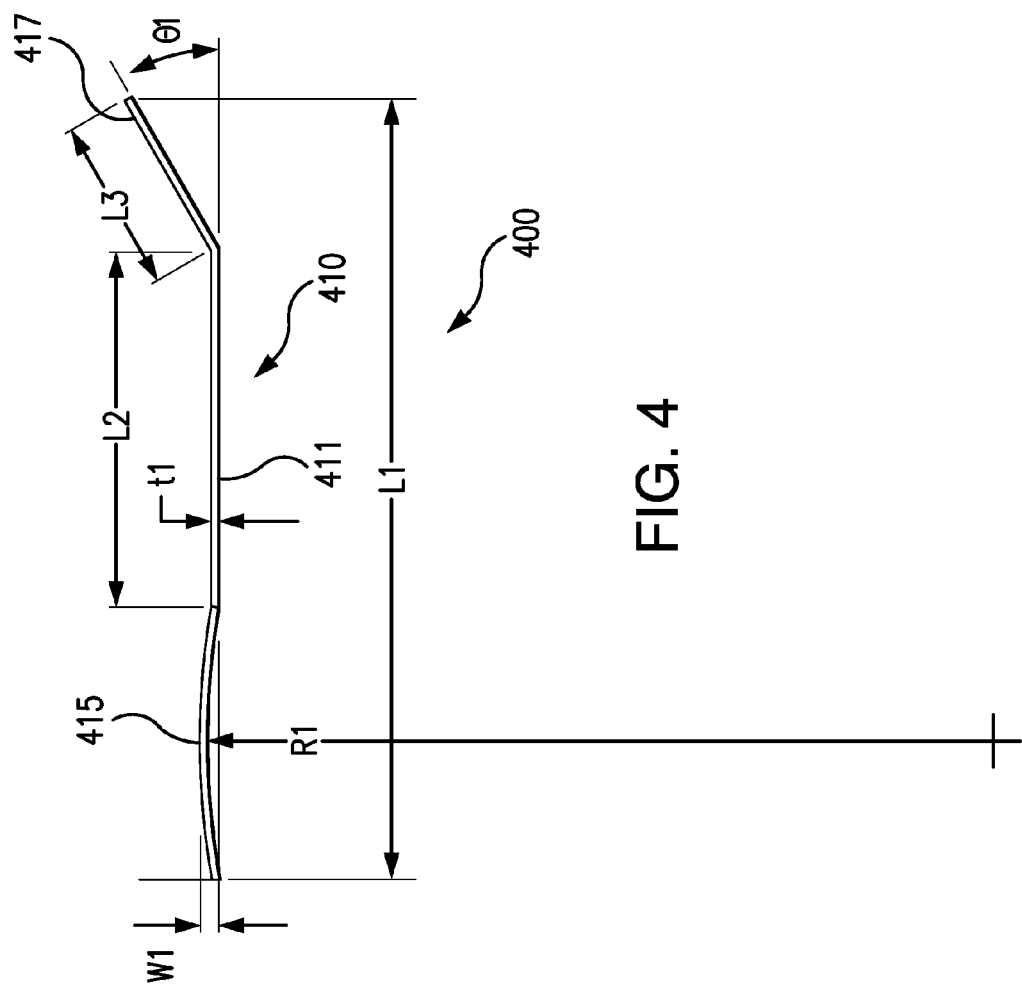
FIGS. 4 and 5 are side views of example shaft constructions of surgical hand instruments in accordance with the invention, having arcuately curved distal shaft portions combined with proximal bends formed in the shafts thereof.

Although variations in the specific dimensions are possible, and contemplated by applicants, as illustrated in FIG. 4, the overall length L1 of the instrument 400 is about 45 cm. The length L3 of the angularly offset proximal shaft portion 417 is about 10 cm. The length L2 of the main shaft 411 is about 20 cm. The radius R1 of the arcuately curved portion 415 is about 45 cm. The shaft thickness t1 is about 0.5 cm, and the width W1 of the shaft 410, taking into account the added width due to the arcuate portion 415 is about 1.2 cm. The angle θ1 between the axis of the main shaft portion 411 and the proximal angularly offset portion 417 is about 30 degrees. Naturally, these values are for the purpose of providing an example, and the instrument can be embodied with actual values that differ slightly or greatly from the foregoing values.

Figure 5:
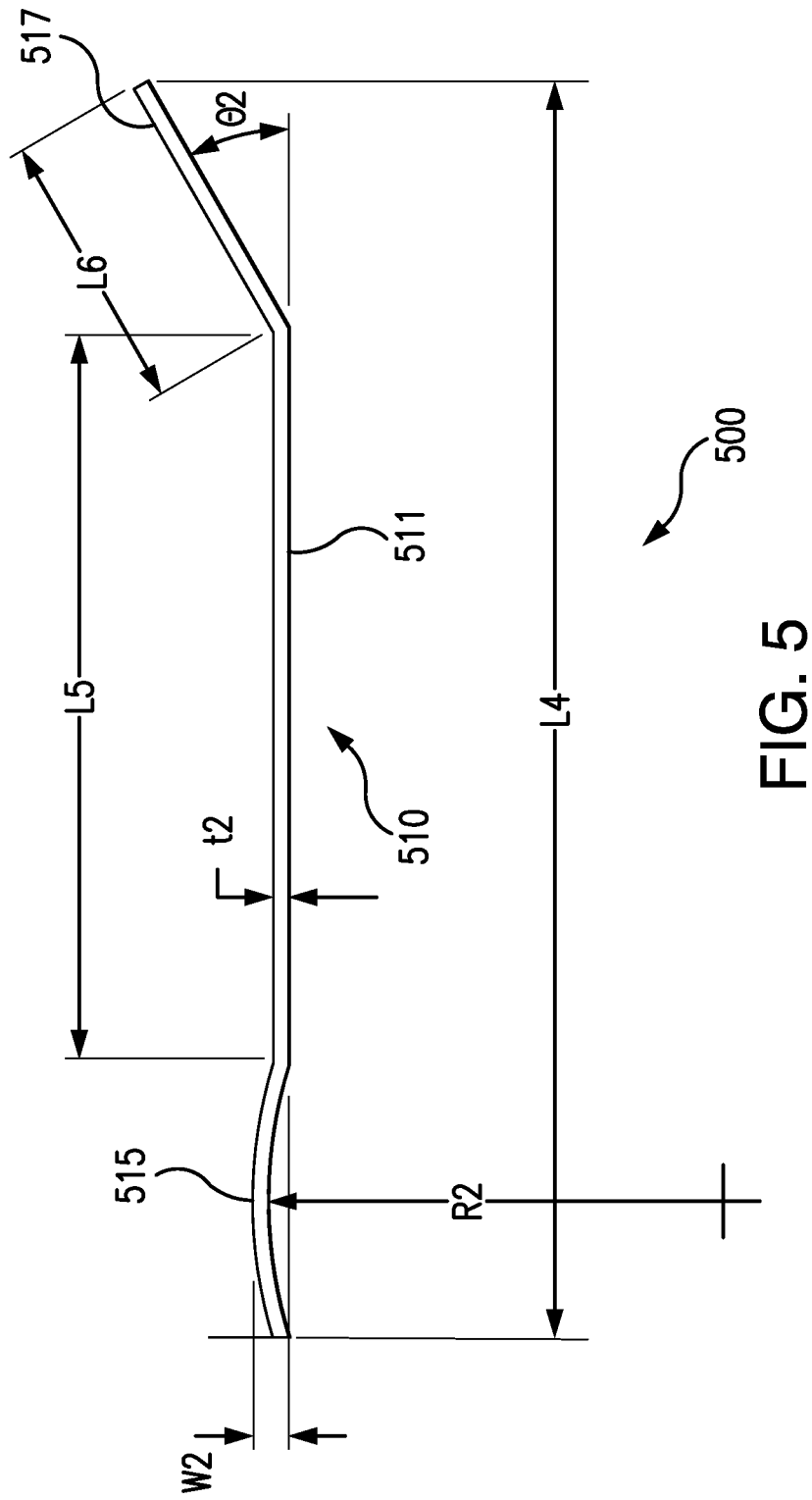

The embodiment of the surgical instrument 500 illustrated in FIG. 5 is similar to the embodiment of FIG. 4, but with a more shallow curvature being provided to the distal curved portion 515 of the shaft 510. The overall length L4 of the instrument 500 is about 45 cm. The length of the angularly offset proximal shaft portion 517 is about 10 cm. The length L5 of the main shaft 511 is about 26 cm. The radius R2 of the arcuately curved portion 515 is about 16.5 cm. The shaft thickness t2 is about 0.5 cm, and the width W2 of the shaft 510, taking into account the added width due to the arcuate portion 515 is about 1.25 cm. The angle θ2 between the axis of the main shaft portion 511 and the proximal angularly offset portion 517 is about 30 degrees. Naturally, these values are for the purpose of providing an example, and the instrument can be embodied with actual values that differ slightly or greatly from the foregoing values.

Figure 6A:
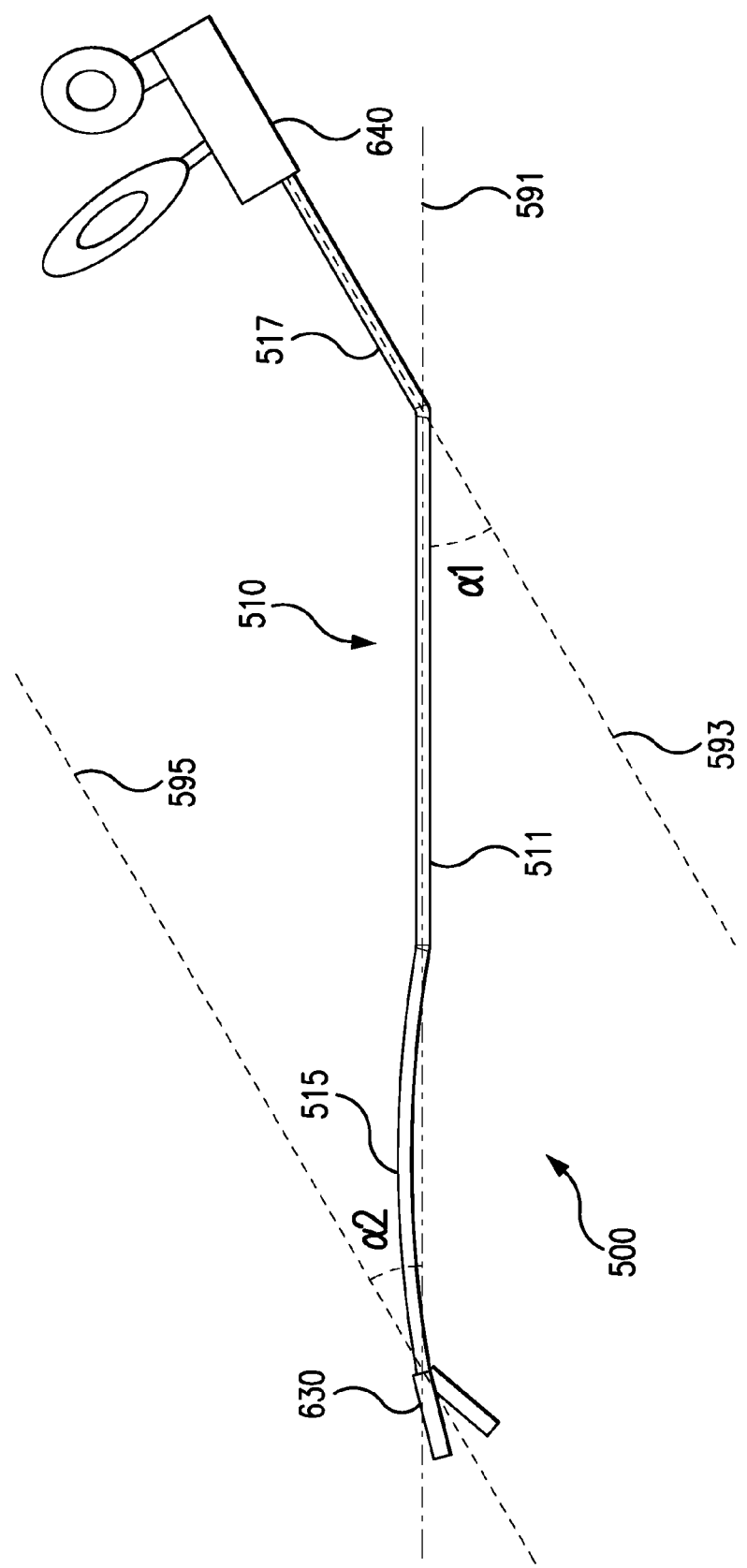
FIG. 6A is a side view of a surgical hand instrument in accordance with the invention having a shaft construction having an arcuately curved distal shaft portion combined with proximal bend formed in the shaft thereof.
Figure 6B:
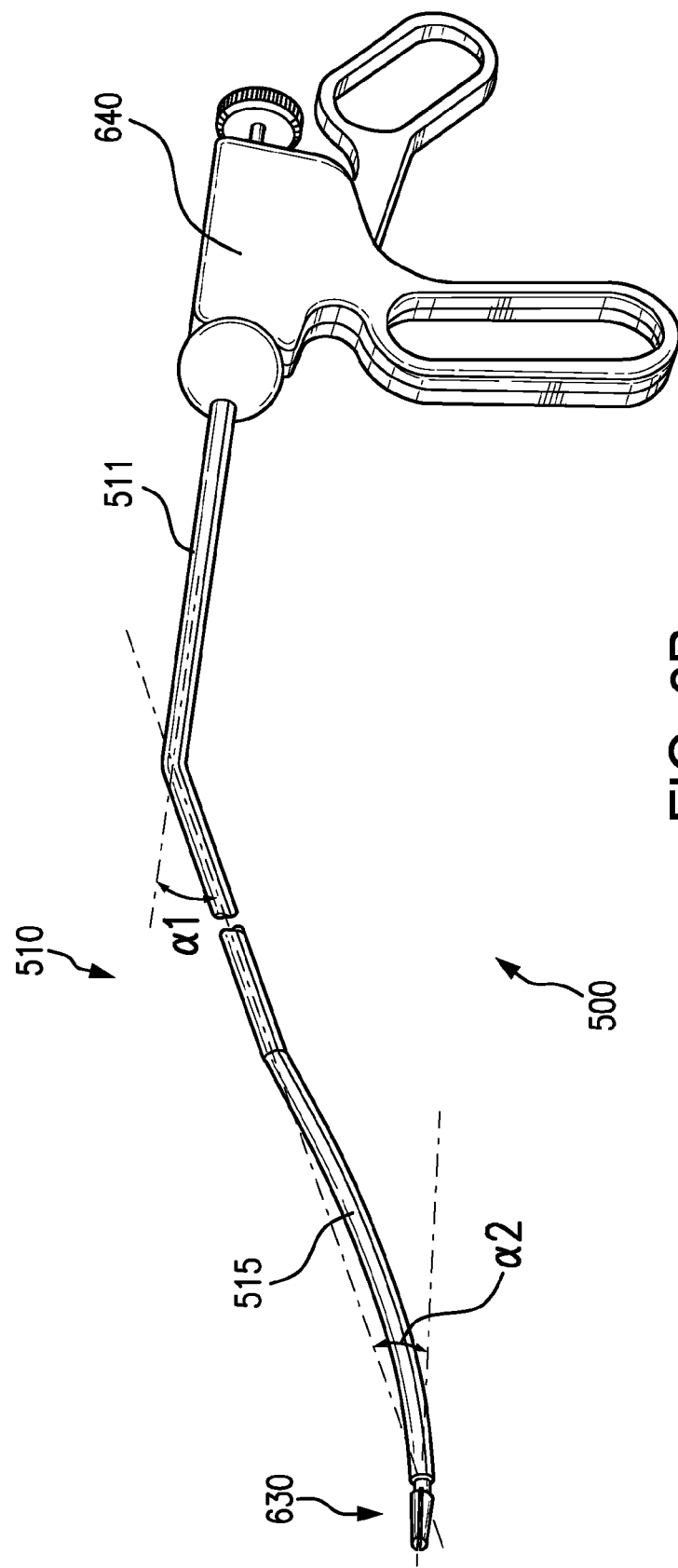
FIG. 6B is an isometric view of the surgical hand instrument of FIG. 6A.

In accordance with one aspect of the invention, and as illustrated for example in FIGS. 6A and 6B, the relative angle α1 (alpha 1) between the central axis 591 of the instrument 500 and the angularly offset proximal shaft portion 517 is about the same as the relative angle α2 (alpha 2) between an axis 595 of the effector end 630 and the central axis 591 of the instrument 500. In accordance with one preferred embodiment, the angles α1, α2 are each about 30 degrees. Naturally, however, the angles α1, α2 can vary from that magnitude as desired or required. Moreover, the angles can be embodied such that they are adjustable. This can be accomplished by utilizing malleable materials and/or through use of an angularly adjustable shaft 510.

If so desired, the proximal handle 640 can be formed so as to have an angular offset, with respect to the proximal shaft portion 517, in order to augment the relative angle formed between the main shaft 511 and the proximal shaft portion 517. Further, angular adjustability can be provided at this point as well, to allow the user to determine the most comfortable position for the handle 640.

FIG. 7 illustrates two laparoscopic surgical instruments 500 designed and constructed in accordance with the invention, and as described above in connection with FIGS. 5, 6A and 6B. As can be seen, both surgical instruments 500 are inserted though an access port 770, which in-turn, in use would ordinarily be inserted through an incision formed in a patient, typically through the patient's abdominal wall, for example.

As illustrated, a relative angle β1 is formed between the proximal angularly offset portions 517 of the shafts thereof, as is a relative angle β2 formed between the axes of the distal effector ends 630. Although these angles can be any particular value needed or desired, in accordance with one aspect of the invention, these angles are about the same, and range between about 30 and about 60 degrees. In accordance with one embodiment, the angles β1, β2 are about 45 degrees.

Instruments designed and constructed in accordance with the invention, used in conjunction as illustrated in FIG. 7, or with conventional laparoscopic instruments, allow for reduced interference between the instruments being used. In use, there is a reduced need for manipulating instruments so that they cross the central axis of the access device 770. This advantageously reduces the obstruction of the surgeon's view through an endoscope or other viewing device. Additionally, the separation of the handles 640 afforded by the angularly offset proximal portion 517 of the shaft 510, in combination with an advantageous orientation between the effector ends 630, reduces or completely eliminates the need for a surgeon to cross his or her arms while performing a procedure.

In use, the perception by the surgeon is, to an extent, as if the surgical site were open, located at the intersection of the proximal angularly offset portions of the instrument shaft, but displaced vertically therefrom. Accordingly, the movements of the surgeon need not be substantially different from those he or she would use when performing an open surgery. Therefore, the difficulty level is reduced and the speed of training is increased. Additionally, because of the ergonomically advantageous position of the handles 517 with respect to the patient, fatigue on the surgeon is reduced.

In accordance with the invention, the handle 517 can actuate the effector end 630 in any suitable manner. The handle 517 is preferably connected to the effector end by way of an actuating element that is capable of exerting tension and/or compression without buckling or fatiguing during the life of the instrument. Such element is also preferably somewhat flexible to allow passage through bent and/or curved portions of the shaft, as will be discussed in more detail below.

The actuating element can be of any suitable material, but is preferably formed of a flexible metal or semi-rigid polymeric material. The actuating element can be substantially rod shaped, and can have a substantially circular cross section, for example. The actuating element can be a soft metal rod, such as one formed of a flexible metal alloy. Alternatively, the actuating element can be a semi-rigid coil, which is relatively stiff in resistance to axially-applied forces, but which allows movement through the bends and curves formed in the surgical instrument. The cross section, moreover can be either solid or tubular, as required for strength. The actuating element can be formed wholly or in part by a braided material, such as a braided cable made of a metal or polymer. The actuating element can also be restrained laterally to reduce buckling of the element laterally in compression.

FIGS. 8A, 8B, 8C, 9A, 9B and 9C illustrate side and isometric views of surgical instruments 800, 900, in open and closed positions, respectively. As illustrated, surgical instruments 800 and 900 differ in that the internal angle γ1, γ2 (gamma 1, gamma 2) between an axis of the main shaft 811, 911 of the instrument and the effector ends 830, 930, respectively, is more acute in the instrument 900 of FIGS. 9A-9C. That is, γ2 is less than γ1, as illustrated. In accordance with the invention, preferred fixed angles for γ1 and γ2 are between about 90 degrees and 180 degrees. In still further preferred embodiments, the fixed angles (γ1, γ2) are between about 130 and 155 degrees. In still preferred embodiments, one or more of the fixed angles (γ1, γ2) is about 135 degrees, and in still other preferred embodiments, one or more of the fixed angles (γ1, γ2) is about 150 degrees.

In accordance with a preferred aspect of the invention, as illustrated in FIGS. 8A-8C and 9A-9C, for example, the actuating element 860 can be a compound element. As illustrated, the actuating element 860 includes multiple coupled sections including a first linear element 860a, a first flexible element 860b, and a second linear element 860c. If a curved distal shaft portion is provided, as with the embodiments of FIGS. 4 and 5 for example, further flexible portions can be provided as needed. Coupling of linear and flexible elements can be effected in any suitable manner, including but not limited to use of a cuff, sleeve or spline, for example. Alternatively, if the materials used are compatible, welding, such as solvent, heat or arc welding, brazing, gluing (as with an adhesive or the like), or other suitable techniques can be used.

In accordance with the invention, and as set forth above, the flexible elements (e.g. 860b) can be formed from a suitable flexible material, which can include a solid, tubular, coiled or braided element, for example. In accordance with a preferred aspect, the flexible elements include sufficient flexural and/or torsional rigidity to efficiently transfer forces between the handle 840 and the effector 830 without buckling or twisting while still allowing for bending when urged longitudinally through one or more bends in the shaft 810.

In accordance with the invention, the linear elements (e.g. 860a, 860c) can be of any suitable configuration, and made of any suitable material, including those set forth above. For example, the linear elements 860a, 860c can be solid, tubular, coiled, braided or woven, for example. In accordance with a preferred aspect, the linear elements 860a, 860c are solid or tubular and substantially cylindrical in shape. In any case, the linear elements are preferably relatively stiff in compression, so as to inhibit buckling of the actuating element 860 in compression. If so-embodied, as described in more detail below, the actuating element 860, and particularly the linear elements thereof are also relatively stiff in torsion, so as to provide a relatively quick and accurate response to torsional actuation inputs.

As best seen in the enlarged partial views of the distal end effectors 830, 930 of FIGS. 8A-8C and 9A-9C, the shaft of the actuating element 860 terminates at a link 867, connected thereto with a first pivot 866, such as a pin, which is connected to jaws 831 by way of a second pivot 868. The jaws 831 are closed with respect to one another by exerting a proximally-directed force on the second pivot 868. The proximally-directed force pulls the actuating elements proximally (toward the left in the figures), causing the jaws 831 to ride on a axially stationary cam pin 873, by virtue of cam slots 835 defined in the jaws 831. Accordingly, there is a slight proximal movement of the jaws 831 when they are closed.

Figure 8C:
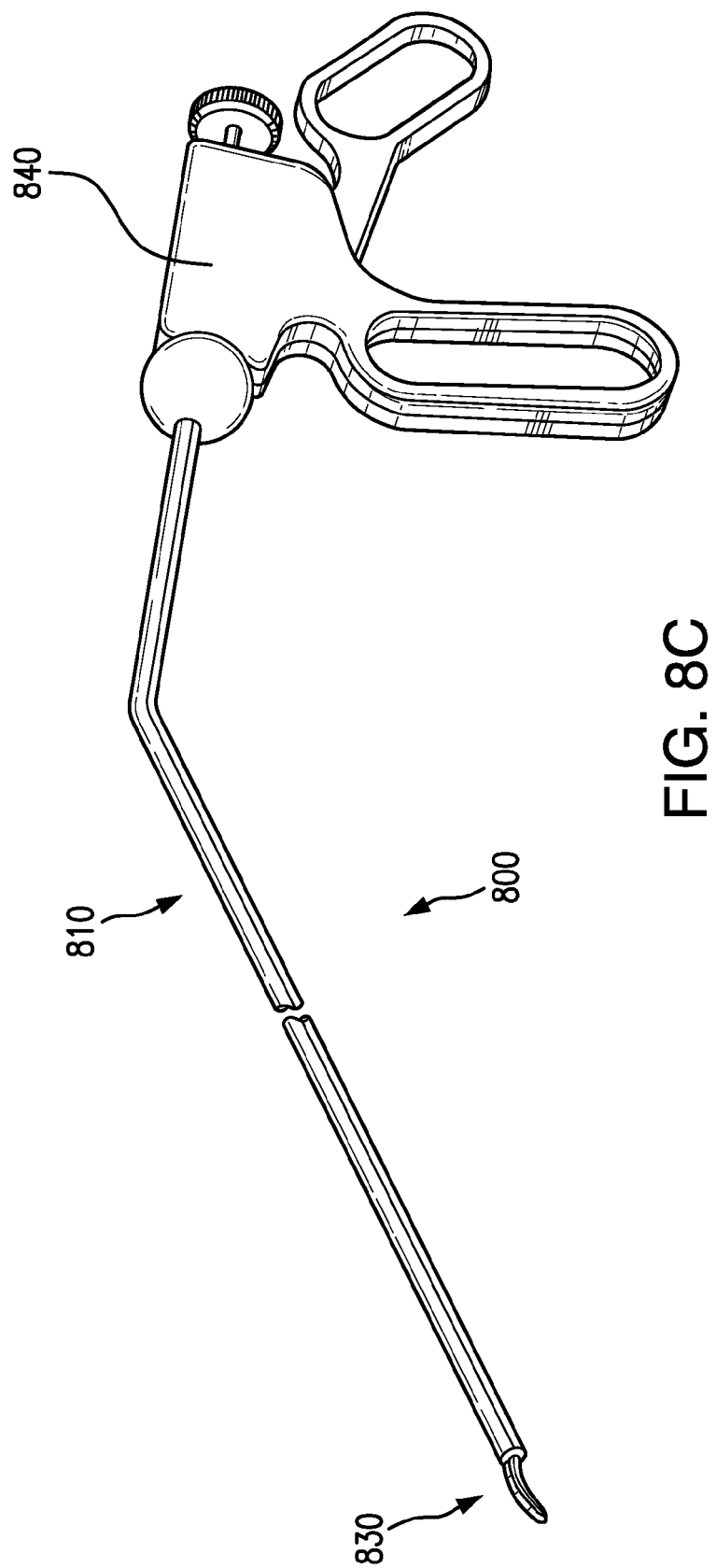
FIG. 8C is an isometric view of the surgical instrument of FIGS. 8A and 8B.

As mentioned briefly above, in the embodiments of FIGS. 8A-8C and 9A-9C, the effectors 830, 930 of the instrument 800, 900 are supported by a distal elbow housing 870, 970. The elbow housing can be preformed with a desired bend, with the relative angle γ between the straight shaft 811 and effector being between about 90 and 180 degrees. In the embodiment of FIGS. 8A and 8B, the angle γ1 is about 150 degrees and in the embodiment of FIGS. 9A-9C, the angle γ2 is about 135 degrees. Alternatively, the distal housing 870 can be essentially straight, and the effectors 830, 930 can be configures to articulate angularly toward and away from the axis of the instrument.

The cam pin 873 can be integrally formed or otherwise mounted in the distal elbow housing 870. Moreover, the distal elbow housing 870 can be adapted to be rotatable with respect to an axis of the shaft 811. Accordingly, the housing 870 can be secured to a tubular member provided on top of or within a skeletal shaft of the instrument 800, 900.

Figure 10:
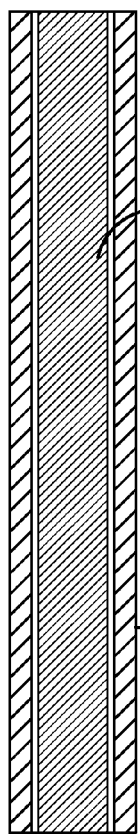
FIGS. 10-12 are cross-sectional views of example shaft constructions for surgical instruments in accordance with the invention.

FIG. 10 illustrates a simple shaft construction in which an outer tubular shaft 1012 acts as a skeleton for an instrument (e.g. instrument 800) in accordance with the invention, helping the instrument maintain its shape, including any bends, curves or other features. The shaft of the actuating element 860 is arranged within a lumen of the tubular shaft 1012, and can be adapted for axial and/or rotational movement, relative to the tubular shaft 1012, depending on the precise embodiment. As set forth above, the actuating element can be solid or tubular, for example, and can be formed from an extruded, coiled, braided, woven or formed of another suitable construction.

Figure 11:
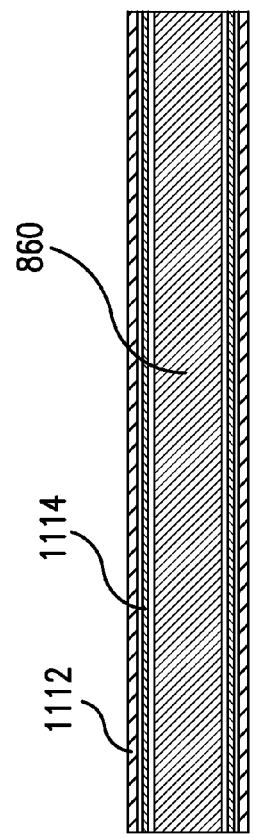

FIG. 11 illustrates a shaft construction adapted to permit axial rotation of a distal component, such as the distal housing 870, for example. In the shaft construction of FIG. 11, an outer tubular shaft 1112 serves as a skeleton for an instrument to maintain its shape. The tubular shaft 1112 is again provided on the outer surface, as with the embodiment of FIG. 10, but an inner rotatable sleeve 1114 is provided and is connected to the distal housing 870 for effecting rotation thereof. The connection can be made in any suitable manner, depending on the material selection. The inner sleeve 1114 can be formed of a polymeric material, or alternatively, another suitable material such as a resilient metal can be used. In this embodiment, the actuating element 860 resides axially internal to the rotatable sleeve 1114. Accordingly, friction and/or interference-reducing elements can be incorporated, including but not limited to spacer bushings placed between concentric elements, low friction materials, and/or one or more decoupling sleeves to reduce interference between adjacent active components, which sleeve(s) may be made of or coated with a low friction material such as PTFE, for example.

Figure 12:
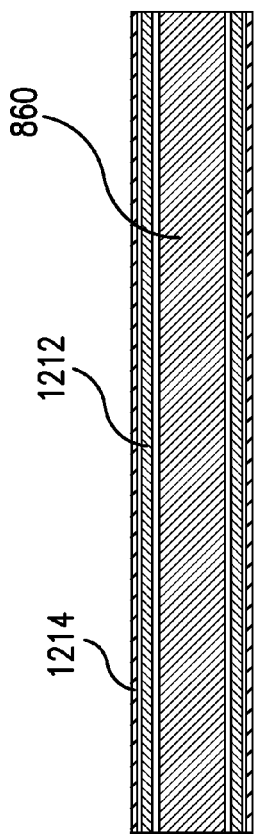

Alternatively, as illustrated in FIG. 12, a shaft construction adapted to permit rotation of a distal component can include a tubular shaft 1212 serving as a shape-maintaining skeleton arranged intermediate the actuating element 860 for actuating the effector end 830, and an outer sleeve 1214 connected to the distal housing 870 for effecting rotation thereof. In such an embodiment, a distal housing can be rotationally coupled to the outer sleeve 1214, while being supported by the inner tubular shaft 1212. As shown in the enlarged partial views of FIGS. 8A-9B, the distal housings 870, 970 can include an axially inwardly-directed annular boss 879 to maintain the position of the housing 870, while the outer sleeve 1214 is rotationally coupled to the housing 870.

FIGS. 13A-13B, 14A-14B and 15A-15B illustrate respective example shaft constructions in accordance with the invention, shown in cross-section at a bend in the shaft through which the respective actuating element 860 passes. FIGS. 13A-13B illustrate an actuating element 860, where the actuating element includes an intermediate flexible portion 1360. The flexible portion allows the actuating element 860 to transmit forces across the illustrated bend or other non-linear region, for example. The flexible portion 1360 can be a flexible solid material, a flexible tubular material, or a woven or braided material, for example. The flexible portion 1360 can be a polymeric, metallic, composite or other suitable material. As illustrated in FIGS. 14A-14B, a flexible portion 1460 is a coiled material, and as illustrated in FIGS. 15A-15B, the entire actuating element is formed of a material and construction that is sufficiently flexible so as to allow the transmission of longitudinal and/or rotational forces therethrough. With any of the foregoing shaft constructions and elements thereof, materials used are selected so as to have appropriate strength and flexibility, and can be formed of polymeric, metal, ceramic or composite materials, for example. Such materials can include but are not limited to metals and metal alloys including steel, titanium alloys, nickel alloys, copper alloys, shape memory alloys such as nitinol, polymers such as PTFE, polyethylene, polyurethane, composites such as fiberglass, carbon fiber materials, and the like.

Referring again to FIGS. 8A-9B, for the purpose of providing an example, a first knob 849 or other actuator can be provided in the handle 840 and coupled to an element such as the outer sleeve 1212 to allow manipulation thereof by the surgeon. It is conceived that the internal actuating element 860 is connected to the movable handle portion 841 by way of a lever arrangement, and engaged therewith by way of a spool-shaped bushing 843 or other suitable connection. An adjustable stop 847 can be provided on the proximal end of the handle 840 as an extension of the internal actuating element 860, to maintain or limit the movement of the actuating element 860, and thus the effector 830. The adjustable stop 847 can be positioned to maintain the effector in a closed position—that is, "locked" closed. Applicants further conceive that there are alternative modes for achieving the desired relative motion of the moving components of instruments (e.g. 800, 900) of the invention, and the foregoing embodiment is therefore not intended to be exhaustive or limiting in any way.

Figure 9A:
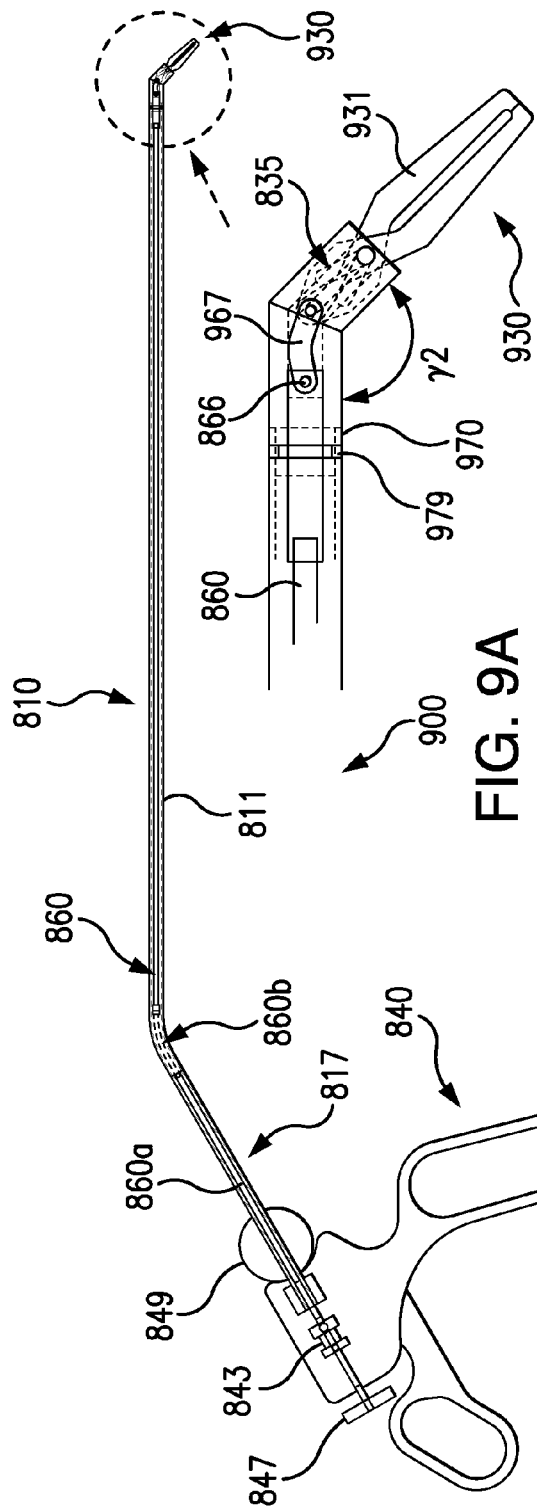
FIGS. 9A and 9B illustrate side and isometric views of a surgical instrument in accordance with the invention, in open and closed positions, respectively.
Figure 9B:
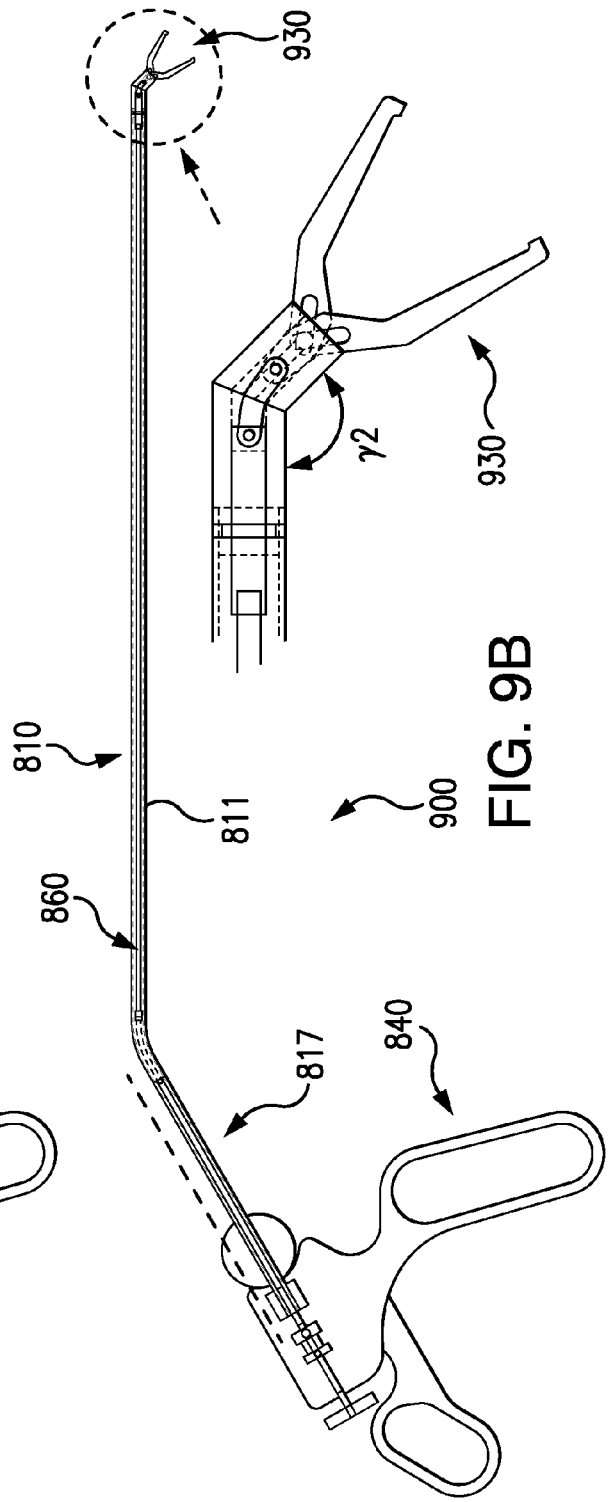
Figure 9C:
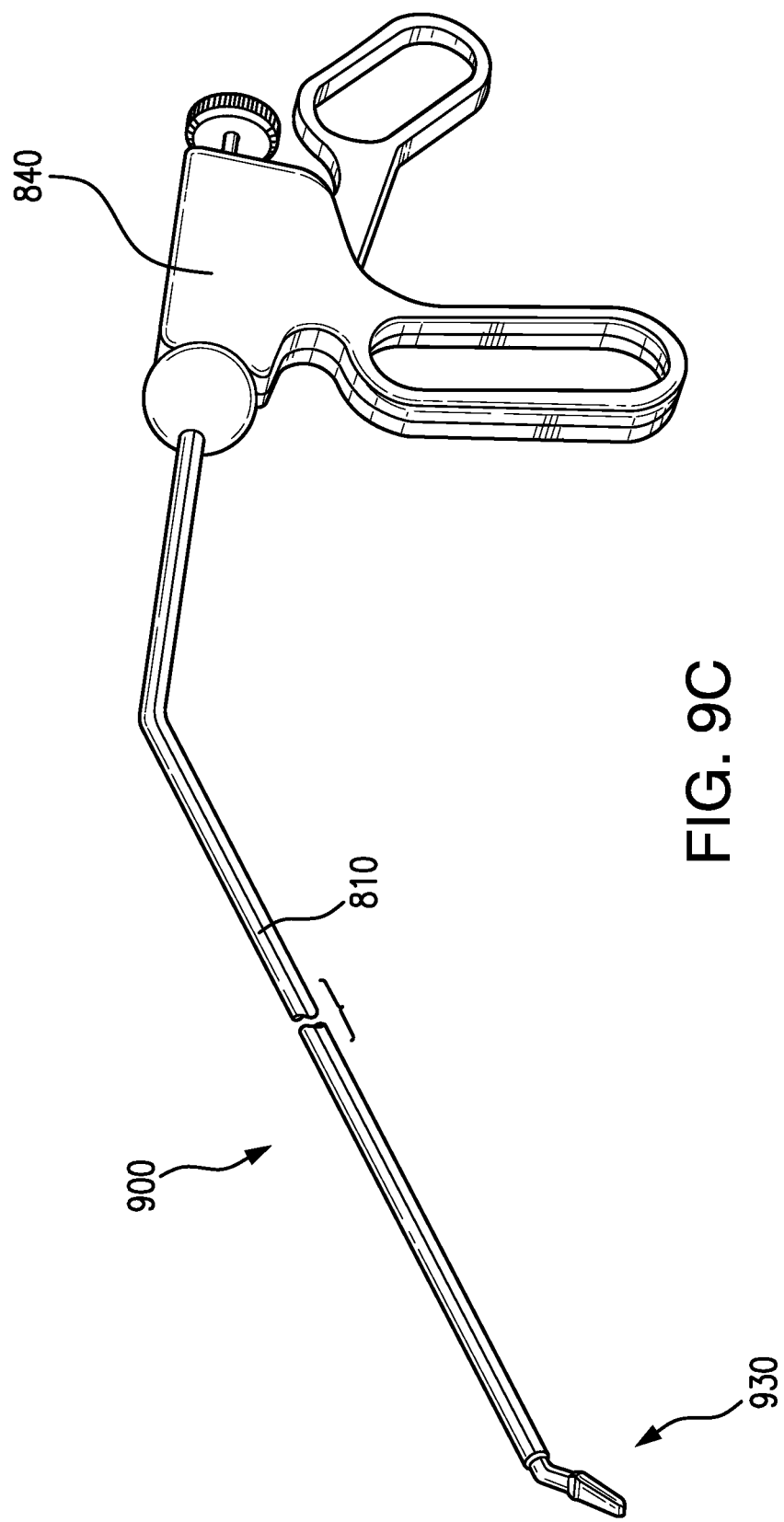
FIG. 9C is an isometric view of the surgical instrument of FIGS. 9A and 9B.

As set forth above, the instrument 900 of FIGS. 9A-9C differs from the instrument 800 of FIGS. 8A-8C primarily in that the bend formed in the distal housing 970 thereof is more extreme (that is, more acute) than in that of the housing 870 of the instrument 800 of FIGS. 8A-8C. Accordingly, the link 967 within the housing 970 is provided with an integral bend to facilitate axial movement through the housing 970. The manner in which the axial movement of the internal actuating element 860 actuates the jaws 931 of the effector 930 is similar to that of the instrument 800 of FIGS. 8A-8C, and as described above.

FIGS. 16-18 illustrate various alternative handle and/or effector configurations for surgical instruments, in accordance with the invention. FIG. 16 illustrates an instrument 1300 having a fixed angle effector 1630, arranged at about 90 degrees with respect to the instrument shaft 1610. The handle 1640 of the instrument 1600 is elongated to provide mechanical advantage to the user. A ratchet mechanism is optionally incorporated into the instrument to reduce fatigue of the surgeon.

FIG. 17 illustrates a laparoscopic surgical instrument 1700 having a switch 1749 arranged in a handle 1740, which switch operates the effector 1730 by way of electrical, electro-pneumatic, or pneumatic actuation, for example. Use of an external source of energy (e.g. electrical or pneumatic) can be implemented to reduce surgeon fatigue. A relatively small force applied by the surgeon thus results in a potentially strong force at the effector 1730. In accordance with one embodiment of this aspect of the invention, the switch 1749 activates a solenoid to allow pressurized gas to enter a cylinder. The pressure urges a piston axially to actuate the effector 1730.

FIG. 18 illustrates two instruments 1800a, 1800b having elongated actuating levers 1840a, 1840b, respectively to provide a mechanical advantage to the surgeon to reduce fatigue. The orientation of the levers 1840a, 1840b also reduces the overall sizes of the instrument handles, reducing interference between adjacent instruments.

The devices and methods of the present invention, as described above and shown in the drawings, provide instruments and surgical procedures that are versatile and facilitate use of multiple instruments in a confined space and through a single access port, if necessary or desired. It will be apparent to those skilled in the art that various modifications and variations can be made to the devices of the present invention without departing from the spirit or scope of the invention. Thus, it is intended that the present invention include such modifications not specifically set forth herein.

What is claimed is:

1. A laparoscopic surgical instrument comprising:
a) a tubular body portion having a primary section defining a longitudinal axis, an angularly offset proximal section defining a proximal axis extending at an obtuse angle to the longitudinal axis of the primary section, and a distal housing section;
b) an end effector operatively associated with the distal housing section of the tubular body portion for performing a surgical task, the end effector including a pair of cooperating jaw members, a dynamic pivot pin connecting the jaw members to one another, and a stationary cam pin supported within the distal housing section and positioned within oppositely angled cam slots formed in the jaw members;
c) a handle assembly operatively associated with the proximal section of the tubular body portion for actuating the end effector; and
d) an actuation shaft extending through the tubular body portion and configured to transfer force between the handle assembly and the end effector, the actuation shaft extending to a distal link connected to the dynamic pivot pin of the end effector, wherein linear movement of the distal link within the distal housing section causes corresponding linear movement of the dynamic pivot pin and jaws members relative to the stationary cam pin, causing the jaw members to move between open and closed positions.

2. A laparoscopic surgical instrument as recited in claim 1, wherein the actuation shaft includes a plurality of coupled sections, including a first linear element extending through the offset proximal section of the tubular body portion, a second linear element extending through the primary section of the tubular body portion, and a flexible element extending between the first and second linear elements.

3. A laparoscopic surgical instrument as recited in claim 2, wherein the flexible element of the actuation shaft is a coiled element.

4. A laparoscopic surgical instrument as recited in claim 2, wherein the flexible element of the actuation shaft is a solid tubular element.

5. A laparoscopic surgical instrument as recited in claim 2, wherein the flexible element of the actuation shaft is one of a woven and braided element.

6. A laparoscopic surgical instrument as recited in claim 1, wherein the actuation shaft includes at least a flexible section extending between the angularly offset proximal section of the tubular body portion and the primary section of the tubular body portion.

7. A laparoscopic surgical instrument as recited in claim 6, wherein the entire actuation shaft is formed from a flexible material.

8. A laparoscopic surgical instrument as recited in claim 1, wherein the distal housing section of the tubular body portion is angularly offset from the primary section of the tubular body portion and defines a distal axis extending at an obtuse angle to the longitudinal axis of the primary section of the tubular body portion of about between 135° and 150°.

9. A laparoscopic surgical instrument as recited in claim 1, wherein the distal housing section of the tubular body portion is adapted and configured to articulate angularly toward and away from the primary section of the tubular body portion.

10. A laparoscopic surgical instrument comprising:
a) a tubular body portion having a primary section defining a longitudinal axis, an angularly offset proximal section defining a proximal axis extending at an obtuse angle to the longitudinal axis of the primary section, and a distal housing section angularly offset from the primary section defining a distal axis extending at an obtuse angle to the longitudinal axis of the primary section;
b) an end effector operatively associated with the distal housing section of the tubular body portion for performing a surgical task, the end effector including a pair of cooperating jaw members, a dynamic pivot pin connecting the jaw members to one another, and a stationary cam pin supported within the distal housing section and positioned within oppositely angled cam slots formed in the jaw members;
c) a handle assembly operatively associated with the proximal section of the tubular body portion for actuating the end effector; and
d) a flexible actuation shaft extending through the tubular body portion and configured to transfer force between the handle assembly and the end effector, the actuation shaft extending to a distal link connected to the dynamic pivot pin of the end effector, wherein linear movement of the distal link within the distal housing section causes corresponding linear movement of the dynamic pivot pin and jaws members relative to the stationary cam pin, causing the jaw members to move between open and closed positions.

11. A laparoscopic surgical instrument as recited in claim 10, wherein the actuation shaft includes a plurality of coupled sections, including a first linear element extending through the offset proximal section of the tubular body portion, a second linear element extending through the primary section of the tubular body portion, and a flexible element extending between the first and second linear elements.

12. A laparoscopic surgical instrument as recited in claim 11, wherein the second linear element of the actuating shaft terminates at the distal link.

13. A laparoscopic surgical instrument as recited in claim 10, wherein the actuation shaft includes at least a flexible section extending between the angularly offset proximal section of the tubular body portion and the primary section of the tubular body portion.

14. A laparoscopic surgical instrument as recited in claim 10, wherein the distal housing section of the tubular body portion is angularly offset from the primary section of the tubular body portion at an angle of about between 135° and 150°.

* * * * *